(12) United States Patent
Ghavami-Nasr et al.

(10) Patent No.: US 9,284,112 B2
(45) Date of Patent: Mar. 15, 2016

(54) AEROSOL SPRAY DEVICE

(75) Inventors: Ghasem Ghavami-Nasr, Salford (GB);
Andrew John Yule, Salford (GB);
Martin Laurence Burby, Salford (GB)

(73) Assignee: The Salford Valve Company Limited (GB)

( * ) Notice: Subject to any disclaimer, the term of this patent is extended or adjusted under 35 U.S.C. 154(b) by 894 days.

(21) Appl. No.: 12/960,896

(22) Filed: Dec. 6, 2010

(65) Prior Publication Data

US 2011/0248099 A1    Oct. 13, 2011

(30) Foreign Application Priority Data

Apr. 13, 2010    (GB) .................................. 1006080.4

(51) Int. Cl.
| | | |
|---|---|---|
| B65D 83/48 | (2006.01) | |
| B65D 83/14 | (2006.01) | |
| B65D 83/20 | (2006.01) | |
| A61L 9/14 | (2006.01) | |
| B05B 1/34 | (2006.01) | |

(52) U.S. Cl.
CPC .............. B65D 83/14 (2013.01); B65D 83/207 (2013.01); B65D 83/48 (2013.01); *A61L 9/14* (2013.01); *B05B 1/3442* (2013.01)

(58) Field of Classification Search
CPC .... B65D 83/682; B65D 83/685; B65D 83/66; B65D 83/663; B65D 83/48
USPC ...................... 251/353; 222/136, 402.18, 137; 239/337, 414; 137/625.4, 625.48, 898
See application file for complete search history.

(56) References Cited

U.S. PATENT DOCUMENTS

| | | | | |
|---|---|---|---|---|
| 3,465,918 | A | * | 9/1969 | Webster ......................... 222/136 |
| 3,465,922 | A | * | 9/1969 | Webster ................... 222/402.18 |
| 3,593,886 | A | * | 7/1971 | Morane ......................... 222/136 |
| 3,653,551 | A | * | 4/1972 | Koch ........................ 222/402.18 |
| 3,674,180 | A | * | 7/1972 | Morane ................... 222/402.18 |
| 3,982,668 | A | * | 9/1976 | Riccio ....................... 222/402.18 |
| 4,117,958 | A | | 10/1978 | Spitzer et al. |
| 4,322,037 | A | | 3/1982 | Heeb et al. |

(Continued)

FOREIGN PATENT DOCUMENTS

| | | |
|---|---|---|
| BE | 1003982 A3 | 7/1992 |
| EP | 0 000 688 A2 | 2/1979 |

(Continued)

*Primary Examiner* — Eric Keasel
(74) *Attorney, Agent, or Firm* — Tarolli, Sundheim, Covell & Tummino LLP

(57) ABSTRACT

An aerosol spray device comprising a pressurized or pressurizable container and a spray discharge assembly mounted on the container. The spray discharge assembly comprises a valve stem moveable from a first limit position to a second limit position to effect spray discharge from the device, a spray outlet region having an outlet orifice from which fluid from the container is discharged, and a flow conduit for supplying fluid from the container to the spray outlet region. The flow conduit has at least one first inlet for liquid from the container and at least one second inlet at the same distance along the conduit as the first inlet(s) or downstream of the first inlet(s) for propellant gas from a headspace of the container. A valving arrangement is adapted such that movement of the valve stem from its first to second limit position opens the first and the second inlets to cause a bubble laden flow to be created in the flow conduit and movement of the valve stem back to its first limit position closes the first and the second inlets.

6 Claims, 13 Drawing Sheets

(56) References Cited

U.S. PATENT DOCUMENTS

| | | | |
|---|---|---|---|
| 5,082,652 A | 1/1992 | Mayfield et al. | |
| 5,323,935 A | 6/1994 | Gosselin et al. | |
| 5,735,465 A * | 4/1998 | Laforcade | 239/414 |
| 6,367,711 B1 | 4/2002 | Benoist | |
| 7,040,507 B2 * | 5/2006 | Koike | B65D 83/66 222/402.1 |
| 2004/0144863 A1 | 7/2004 | Kendrick et al. | |

FOREIGN PATENT DOCUMENTS

| | | |
|---|---|---|
| FR | 2 399 282 A1 | 3/1979 |
| GB | 1 122 675 A | 8/1968 |
| JP | 3-157328 A | 7/1991 |
| JP | 10-309502 A | 11/1998 |
| WO | WO-90/05580 A1 | 5/1990 |

* cited by examiner

AEROSOL SPRAY DEVICE

RELATED APPLICATION

This application claims priority from British Patent Application No. GB 1006080.4, filed Apr. 13, 2010, the subject matter of which is incorporated herein by reference.

FIELD OF THE INVENTION

The present invention relates to an aerosol spray device for discharging a liquid product (e.g. a household product such as an air freshener) in the form of a spray. The invention has particular application to aerosol spray devices which utilise a compressed gas propellant rather than a liquefied gas propellant.

BACKGROUND TO INVENTION

Broadly speaking, aerosol spray devices comprise a container holding a liquid to be discharged together and an outlet nozzle associated with a valving arrangement which is selectively operable to allow discharge of the liquid as a spray from the nozzle by means of the propellant provided within the container.

Both "compressed gas propellant aerosols" and "liquefied gas propellant aerosols" are known. The former incorporate a propellant which is a gas at 25° C. and at a pressure of at least 50 bar (e.g. air, nitrogen or carbon dioxide). Such a gas does not liquefy in the aerosol spray device. On opening of the valving arrangement, the compressed gas "pushes" liquid in the spray device through the aforementioned nozzle that provides for atomisation. There are, in fact, two types of "compressed gas propellant aerosols". In one type, only liquid from the container ("pushed-out" by the compressed gas) is supplied to the outlet nozzle. In the other principal type, a portion of the propellant gas from the container is bled into the liquid being supplied to the nozzle which atomises the resulting two-phase, bubble-laden ("bubbly") flow to produce the spray. This latter format can produce finer sprays than the former.

In contrast, "liquefied gas propellant aerosols" use a propellant which is present (in the aerosol spray device) both in the gaseous and liquid phases and is miscible with the latter. The propellant may, for example, be butane, propane or a mixture thereof. On discharge, the gas phase propellant "propels" the liquid in container (including dissolved, liquid phase propellant through the nozzle).

It is well known that "liquefied gas propellant aerosols" are capable of producing finer sprays than "compressed gas propellant aerosols". This is due to the fact that, in the former, a large proportion of the liquefied gas "flash vaporises" during discharge of liquid from the aerosol spray device and this rapid expansion gives rise to a fine spray. Such fine sprays cannot generally be achieved with "compressed gas propellant aerosols", in either of the two principal formats described above.

Attempts have been made to improve the "fineness" of sprays generated by "compressed gas propellant aerosols". Prior art proposals have included the possibility of "bleeding off" some of the compressed gas (e.g. nitrogen) that is present in the container and mixing this with the liquid product to achieve "two fluid atomisation" which is a technique known to provide fine sprays for other areas of spray technology, e.g. liquid fuel combustion. However it has been found extremely difficult to produce fine sprays using two fluid atomisation with aerosol spray devices, and the nearest approach has been to use the equivalent of a vapour phase tap (VPTs are used in "liquefied gas propellant aerosols") to bleed some gas into the valve. However results for improving spray fineness have not been significantly beneficial.

WO 90/05580 (Weston et al) discloses a discharge valve for regulating the flow of a liquid product from an aerosol canister pressurised by a permanent gas propellant such as nitrogen. The discharge valve incorporates a valve stem moveable from a first limit position to a second limit position to effect spray discharge from the device via a spray outlet region thereof. The valve stem is formed with a flow conduit (designated as a "mixing chamber") formed with at least one upstream liquid orifice and at least one downstream gas orifice. The discharge valve incorporates a valving arrangement such that movement of the valve stem from its first to second limit position opens the liquid and gas orifices to cause a liquid/gas mixture to be produced in the mixing chamber. Table 1 of WO 90/05580 gives exemplary dimensions for the cross-sections of the mixing chamber, liquid and gas orifices but without detailed consideration as to the relative sizes thereof.

Downstream of the mixing chamber of the device of WO 90/05580 is at least one restrictor through which the mixture is forced to pass to produce a choked or sonic flow, resulting in the mixture expanding to form a "foamy mixture" which passes to an exit orifice at the spray outlet region for discharge from the spray device. The restrictors are employed in the aerosol spray device of WO 90/05580 to ensure that the spray from the exit orifice is essentially constant throughout the discharge of the liquid content of the device. This is achieved by ensuring that the residual pressure which remains across each restrictor when the liquid content of the device is about to become exhausted is still sufficiently high to produce at least substantially choked flow through the or each restrictor and thereby produce a shockwave after each restrictor. More specifically, the flow becomes supersonic downstream of the restrictor and shockwaves are produced as the flow subsequently goes from supersonic to subsonic resulting in vigorous break-up of gas particles to produce a uniform foam. However the need to provide the restrictors results in a relatively complicated construction and a discharge assembly which cannot readily be produced by mass-production techniques such as injection moulding.

Copending U.S. Patent Application No. 61/261,906 discloses an aerosol spray device for producing fine sprays in the case of "compressed gas propellant aerosols" although there is some applicability to "liquefied gas propellant aerosols". Embodiments disclosed in the prior US application incorporate a spray discharge assembly incorporating a flow conduit for supplying fluid from a container to a spray outlet region of the device. The flow conduit has at least one first inlet for liquid from the container and at least one second inlet for propellant gas from a head space of the container. The spray discharge assembly further incorporates a valving arrangement such that movement of a valve stem from a first to second limit position opens the first and second inlets to cause a bubble laden flow to be generated in the flow conduit for supply to the spray outlet region. In accordance with the teaching of the prior US application, there is provided, downstream of the flow conduit, an approach chamber having at least one inlet and an outlet communicating with a discharge orifice. The outlet of the approach chamber (which is effectively an inlet to the discharge orifice) is surrounded by a sharp edge. Located between the flow conduit and the approach channel is at least one jetting orifice through which the bubble laden flow from the flow conduit passes and issues as a jet into the approach channel, the jetting orifice being configured for directing the jets against the sharp edge. The invention of the prior US application was found to produce fine sprays as a result of a separation and reattachment phenomenon of the bubble laden flow in the discharge orifice.

SUMMARY OF THE INVENTION

According to a first aspect of the present invention there is provided an aerosol spray device comprising a pressurised or pressurisable container holding a liquid to be discharged from the device by a gaseous propellant that is a gas at a temperature of 25° C. and a pressure of at least 50 bar and a spray discharge assembly mounted on the container, said spray discharge assembly incorporating a valve stem moveable from a first limit position to a second limit position to effect spray discharge from the device, a spray outlet region having an outlet orifice from which fluid from the container is discharged, a flow conduit for supplying fluid from the container to the spray outlet region, said flow conduit having at least one first inlet for liquid from the container and at least one second inlet at the same distance along the conduit as said first inlet(s) or downstream of said first inlet(s) for propellant gas from a headspace of the container, and a valving arrangement adapted such that movement of the valve stem from its first to second limit position opens said first and said second inlets to cause a bubble laden flow to be created in the flow conduit and movement of the valve stem back to its first limit position closes said first and said second inlets, wherein (i) the flow conduit has a cross-sectional area equivalent to a circle with a diameter of 0.5 mm to 1.5 mm at least in the region of the second inlet(s) defined in (iii) below, (ii) the first inlet(s) has/have a total cross-sectional area equivalent to that of a circle with a diameter of 0.15 mm to 1.5 mm with the proviso that at least one first inlet has a cross-sectional area equivalent to that of a circle with a diameter of at least 0.1 mm, and (iii) the second inlet(s) has/have a total cross-sectional area equivalent to that of a circle with a diameter of 0.1 mm to 0.7 mm diameter with the proviso that at least one second inlet has a cross-sectional area equivalent to that of a circle with a diameter of at least 0.10 mm and with the further proviso that the second inlet(s) has/have a total cross-sectional area less than that of the first inlet(s), and (iv) the spray outlet orifice has a cross-sectional area less than the total cross-sectional area of the first inlet(s) and greater than the total cross-sectional area of the second inlet(s).

For the purposes of the above definition, the cross-sectional areas of the first inlet(s) and the second inlet(s) are measured at their point of entry into the flow conduit.

The invention has been based on a finding that by appropriate sizing of the flow conduit and the cross-sectional dimensions of the first (liquid) inlet(s) and second (gas) inlet(s) to the flow conduit, it is possible to produce good sprays from an aerosol spray device without the need to incorporate restrictors as required in the construction of WO 90/05580. This is due to the fact that the relatively small sizes of the first (liquid) inlet(s) and the conduit create a pressure drop within the conduit, and a relatively high fluid velocity in the conduit, which assist in drawing-in gas through the second (gas) inlet(s) to produce a bubble-laden flow which results in discharge of a fine spray from the discharge orifice of the aerosol spray device.

The fact that good sprays are obtained using the device of the invention without the need for the restrictors required in the construction of WO 90/05580 means that the discharge assembly of the present invention readily lends itself to production by injection moulding and with a small number of component parts, comparable or equal in number to the parts used to construct conventional valves for consumer aerosol devices.

By adopting the dimensions as outlined above, aerosol spray devices in accordance with the invention can have a gas/liquid volume flow rate ratio of less than 20, more preferably less than 15 and ideally in the range 6-10 (where the gas volume flow rate is calculated for atmospheric pressure conditions at 20° C.).

The present invention has been found particularly applicable in the case where the spray outlet region comprises a nozzle adapted to impart a swirling motion to the bubble laden flow prior to discharge thereof from the device. The nozzle may be a Mechanical Break-Up Unit, for which further detailed examples are given below. With such units, it has been found that good atomisation of the liquid being discharged is obtained, resulting in a fine spray. Aerosol spray devices in accordance with the invention are eminently suitable for use in conjunction with a variety of consumer products, e.g. air-fresheners, polishes and deodorants.

Preferably the flow conduit is configured for substantially disturbance free flow of said bubble laden flow to the spray outlet region of the device.

The substantially disturbance-free flow of the bubble laden flow can be achieved by configuring the flow conduit such that there is an absence of any flow disturbances, whereby the bubble laden flow is delivered to the spray outlet region in substantially the form in which it was created. Additionally, the valving arrangement present in the aerosol spray device should likewise not have any substantial effect on the bubble laden flow once created. Thus there is preferably no valve or obstruction in the bubble laden flow in between its creation and the spray outlet region of the aerosol spray device.

Preferably the bubble laden flow is such that it comprises a flow of ideally homogenous bubbles, with similar diameter, and without stratification across the flow conduit. Suitable dimensions for the flow conduit and the first and second inlets which enable such a flow to be obtained are given below.

The bubble laden flow should be at a velocity that gives a sufficiently short residence time of the flow in the flow conduit such that bubble coalescence or stratification does not occur. Typically the flow rate should be in the range 0.5 to 5 m/s.

The bubble laden flow should be at between 1 bar and 20 bar pressure, and in a preferred embodiment for a consumer aerosol can, between 4 bar and 12 bar (said pressure reducing during evacuation of the can).

The ratio of volume of gas/volume of liquid contained in the bubble laden flow in the flow conduit should be between 0.2 and 3.0 at the pressure prevailing in this conduit and more preferably between 0.3 and 1.3.

The flow conduit in the aerosol spray device of the invention may be regarded as a mixing chamber. This flow conduit has a cross-sectional area equivalent to that of a circle with a diameter of 0.5 to 1.5 mm, more preferably 0.8 mm to 1.2 mm, as measured at the level of the second (gas) inlet(s). This cross-section may for example be about 1 mm. The conduit may be of uniform and/or circular cross-section along its length. The flow conduit (mixing chamber) may be provided in a valve stem of the aerosol spray device, in which case the first and second inlets are also provided in the valve stem (and communicate with the mixing chamber).

The spray outlet orifice may have a cross-sectional area equivalent to a circle with a diameter of 0.2 mm to 0.7 mm.

The first inlet(s) through which liquid from the container is supplied into the flow conduit preferably enter the flow conduit upstream of the second inlet(s) through which gas from the headspace of the container is bled or otherwise supplied. In an alternative embodiment, the first and second inlets are in the same plane of cross-section of the conduit. There will generally be from 1 to 6 of each of said first and second inlets. The first inlets are ideally of uniform (preferably circular) cross-section and have a total cross-sectional area equivalent to that of a circle with a diameter of 0.15 mm to 1.5 mm, more preferably 0.15 mm to 0.70 mm diameter, even more preferably, for less viscous liquids, 0.3 mm to 0.5 mm diameter. In the case that there is more than one first inlet then at least one such inlet should have a cross-sectional area equivalent to that of a circle with a diameter of at least 0.1 mm.

The second inlets are also ideally of uniform (preferably circular) cross-section and have a total cross-sectional area equivalent to that of a circle with a diameter of 0.1 mm to 0.7 mm, more preferably 0.15 mm to 0.35 mm diameter. In the case that there is more than one second inlet then at least one such inlet should have a cross-sectional area equivalent to that of a circle with a diameter of at least 0.1 mm.

The amount of gas bled through the inlet may be 4 to 8 times the liquid volume, where said gas volume is specified at atmospheric pressure and 20° C. Higher figures may cause the can pressure to reduce quickly and liquid to remain in the can when all can pressure has been depleted, unless the initial fill ratio of the can, which is initial liquid volume divided by total can volume, is reduced below 50%, this being undesirable from the viewpoint of attractiveness of the consumer aerosols to purchasers.

The spray device may incorporate an actuator assembly which is mounted on the valve stem and which incorporates the spray outlet region. In this case, the actuator assembly will incorporate a discharge conduit providing for communication between the flow conduit and the spray outlet region. The flow conduit may be of circular-section as may be the discharge conduit. Preferably the flow and discharge conduits are of identical diameter, ideally in the range 0.5 mm to 1.5 mm. The flow and discharge conduit may each have a length from 3 to 50 times their diameter. The discharge conduit may, throughout its length, be collinear with the flow conduit. Alternatively the discharge conduit may be formed in two sections, namely a first section collinear with the flow conduit and a second section angled (e.g. perpendicular thereto).

Where the flow conduit is provided in a valve stem of the aerosol spray device, with the first and second inlets also provided in the valve stem, the valving arrangement may comprise first and second seals which in the first position of the valve stem close the first and second inlets respectively. Optionally, the valving arrangement comprises two said first seals which in the first position of the valve stem locate one upstream of the first inlet(s) and one downstream thereof.

Alternatively, where the flow conduit is provided in a valve stem of the aerosol spray device, with the first and second inlets also provided in the valve stem, the valving arrangement may comprise a single seal, with said first and second inlet(s) configured to be closed by said single seal.

A lower region of the valve stem may locate within a housing and the or each seal may be mounted on the housing for relative sliding engagement with the valve stem. With such an arrangement, a portion of the housing preferably engages around the valve stem in the region of the second inlet.

The or each seal may be an O-ring.

As indicated above, the invention is particularly effective for spray devices where the spray outlet region comprises a nozzle adapted to impart a swirling motion to the bubble laden flow prior to discharge thereof from the device. The nozzle may be a conventional Mechanical Break-Up unit. Thus, the nozzle, may comprise a discharge orifice, a swirl chamber provided around the discharge orifice and one or more channels ("swirl channels" or "swirl arms") extending outwardly from the swirl chamber. In such an arrangement, the flow conduit is in communication (e.g. via a discharge conduit in an actuator assembly) with the outer end(s) of the channel(s) so that the bubble laden flow is supplied to the swirl chamber for discharge through the orifice.

The discharge orifice of the nozzle may, for example, have a diameter of 0.15-0.5 mm. There may be from 1 to 8 swirl channels each having a width of 0.1 mm-0.5 mm and a depth of 0.1 mm-0.5 mm. The swirl chamber may be circular with a diameter of 0.3 mm to 2 mm.

The nozzle may comprise an insert having a face locating against a face of a boss in the spray outlet region of the device, wherein said discharge orifice is provided in the insert and wherein said faces of the boss and the insert are configured to define the swirl chamber and the channels.

An aerosol device according to the first aspect of the invention may contain a material selected from the group consisting of pharmaceutical, agrochemical, fragrance, air freshener, odour neutraliser, sanitizing agent, polish, insecticide, depilatory chemical (such as calcium thioglycolate), epilatory chemical, cosmetic agent, deodorant, anti-perspirant, anti-bacterial agents, anti-allergenic compounds, and mixtures of two or more thereof. The device may, in particular, contain a pharmaceutical composition, a fragrance composition, an odour neutralizer composition or a depilatory composition.

The flow conduit and valving arrangements employed in the aerosol spray devices of the present invention may, for example, be as shown in FIGS. 3 and 8-10 of the aforementioned U.S. patent application Ser. No. 61/261,906. The present specification does, however, provide details of additional valving/flow conduit arrangements which may be employed in the invention of that earlier U.S. application and in other aerosol spray devices. Therefore, a second aspect of the present invention extends to such valving/flow conduit arrangements.

According to the second aspect of the invention, there is provided a valving arrangement for an aerosol spray device comprising a pressurised or pressurisable container holding a liquid to be discharged from the device by a propellant and a flow conduit for supplying fluid from the container to a spray outlet region, said flow conduit having at least one first inlet for liquid from the container and at least one second inlet at the same distance along the conduit as said first inlet(s) or downstream of said first inlet(s) for propellant gas from a headspace of the container, the valving arrangement comprising:

a valve stem moveable from a first limit position to a second limit position to effect spray discharge from the device; and a single seal configured to close both the first and second inlets when the valve stem is in its first limit position;

wherein movement of the valve stem from its first to its second limit position opens said first and said second inlets to cause a bubble laden flow to be created in the flow conduit and movement of the valve stem back to its first limit position closes said first and said second inlets.

Such a valving arrangement is not limited in application to aerosol spray devices of the type defined in the first aspect of the invention, although they do have particular application thereto. Rather, the valving arrangements of the second aspect of the invention may be applied to any suitable aerosol spray device.

The valving arrangement may further comprising a housing, said housing at least partially defining a liquid flow path connecting the liquid in the container to the first inlet(s) and a separate gas flow path connecting the headspace with the second inlet(s).

As with one embodiment of the first aspect of the invention, a lower region of the valve stem may locate within the housing and the single seal may be mounted on the housing for relative sliding engagement with the valve stem.

In one embodiment, the valving arrangement further comprises a distributor plug mounted immediately below the single seal within the housing and further defining said separate liquid and gas flow paths. The distributor plug may perform a dual function of both defining the separate flow paths and acting as a limit stop for the valve stem.

Alternatively, the single seal may comprise two components: a thin upper gasket mounted on the housing for relative sliding engagement with the valve stem; and a thin lower gasket mounted immediately below the upper gasket within the housing and further defining said separate liquid and gas flow paths. Such an arrangement means that the upper and lower gaskets can be formed from different materials. Moreover, formation of the separate liquid and gas flow paths in the lower gasket may be done simply by forming a channel on one side of the gasket leading to an associated notch through the gasket, and forming a separate notch through the gasket on an opposite side thereof. The thin gaskets may be made by injection moulding. Rather than having discrete adjacent upper and lower gaskets, the upper and lower gaskets may be formed integrally with one another, forming a relatively thick gasket. Such a relatively thick gasket could also be made by injection moulding, by which the flow paths could be defined during moulding.

BRIEF DESCRIPTION OF THE DRAWINGS

The invention will be further described by way of example only with reference to the accompanying drawings, in which:

FIG. 11 is a cross section through A-B of FIG. 9a;

FIG. 13 is a cross section through the valving arrangement of FIG. 12a;

DETAILED DESCRIPTION

Figure 1:
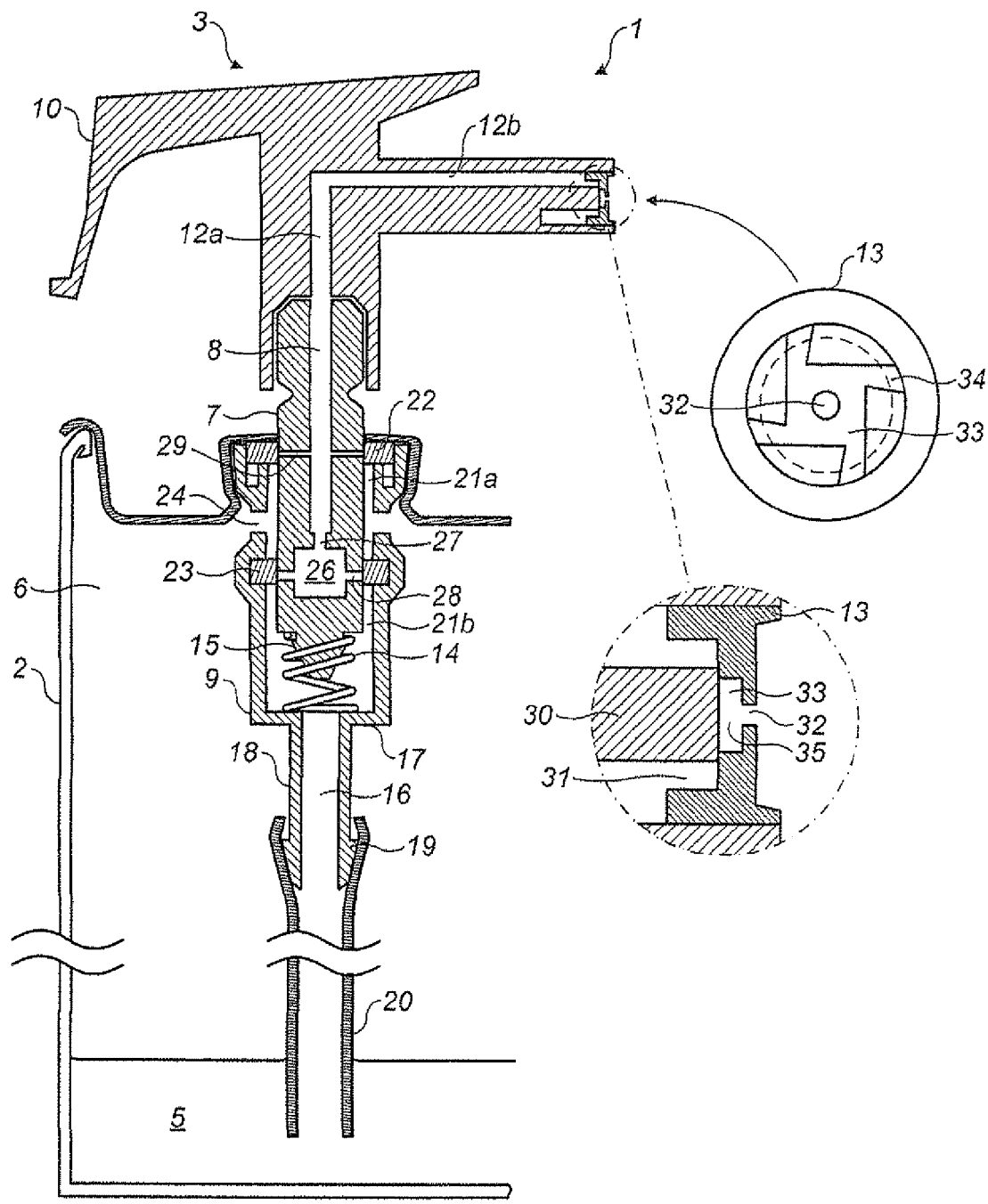
FIG. 1 schematically illustrates a first embodiment of aerosol spray device in accordance with the invention.

FIG. 1 illustrates a first embodiment of aerosol spray device 1 in accordance with the invention in the normal "rest" position. The device 1 comprises a pressurised container 2 on the top of which is mounted an spray discharge assembly 3 which, as schematically illustrated in the drawings, is crimped on to the top portion of container 2. Provided within container 2 is a liquid 5 to be dispensed from the device by a pressurised gas such as nitrogen, air or carbon dioxide which has limited solubility in the liquid 5 and is in a head space 6 of the container 2. The gas in the head space 6 may, for example, be at an initial pressure of 9 to 20 bar depending upon the type of container in use. The initial pressure may, for example, be 9 or 12 bar. There are however higher pressure "standard" cans now available (but as yet little used), for which the initial pressure is for example 18 bar or higher. Such cans can also be used in the present invention. Higher initial can pressure is good because there is more mass of gas available to help atomisation and higher nozzle velocities which also helps atomisation and also the proportionate loss in can pressure as the can empties is less. This helps maintain spray quality and flow rate better during can lifetime.

The valve assembly 3 comprises a generally cylindrical, axially movable valve stem 7 having an axial bore 8 extending from the upper end of valve stem 7 part way towards the lower end thereof. At its lower end, valve stem 7 locates within a cylindrical housing 9 positioned internally of the container 2 and at its upper end is fitted with an actuator in the form of a cap 10 having a spray outlet region 11. This cap 10 (which may be of the type available under the name "Kosmos" from Precision Valve (UK) Ltd) is moulded so as to locate on the top of valve stem 7 and has an internal L-shaped conduit formed as a first section 12a collinear with the bore 8 of valve stem 7 and a second section 12b that extends at right angles to section 12a and leads to spray outlet region 11. Provided at the outlet end of region 11 is a conventional MBU (Mechanical Break-Up Unit) insert 13 which is described in more detail below.

In broad outline, the aerosol spray device 1 is operated by pressing down on the cap 10 to cause downward movement of valve stem 7 with resultant discharge of a spray from spray outlet region 11, the spray being produced in the manner described more fully below.

As shown in the drawings, valve stem 7 is biased upwardly of the container 2 by means of a coil spring 14 locating at its upper end around a lower bulbous nose 15 on the valve stem 7. Lower end of coil spring 14 locates around an aperture 16 in lower wall 17 of the housing 9. Depending from wall 17 is a tubular spigot 18 having a lower wall enlarged end 19 to which is fitted a dip tube 20 which extends to the base of the container 2. It will be appreciated from the drawing that the lower region of container 2 is in communication with the interior of the housing 9 via the dip tube 20, spigot 18 and aperture 16 (which provides a liquid inlet for housing 9).

For reasons which will become clear from the subsequent description, valve stem 7 has an external diameter slightly less than the internal diameter of housing 9 so that an annular clearance 21 is defined between valve stem 7 and housing 9.

Annular gaskets 22 and 23 formed of rubber or other elastomeric material are provided at upper and central regions respectively of the housing 9 and are dimensioned to seal against the outer surface of valve stem 7. To facilitate understanding of the device as further described below, the aforementioned annular clearance is shown as being sub-divided into two sections referenced as 21*a* and 21*b*. Section 21*a* of the annular clearance extends between the two gaskets 22 and 23, whereas section 21*b* of the annular clearance is below the lower gasket 23. Formed in the wall of the housing 9 between the two gaskets 22 and 23 are a plurality of ports 24 which provide for communication between the pressurised gas in the head space 6 and the annular clearance 21*a*.

Internally, valve stem 7 is formed with the flow conduit 8 (extending coaxially along the valve stem 7) and a liquid feed chamber 26 which communicates with the flow conduit 8 via a passageway 27. Flow conduit 8 extends from the upper end of valve stem 7 for over 50% of the length thereof. Chamber 26 is below flow conduit 8 and is of greater diameter than flow conduit 8 but significantly smaller length.

Two liquid feed passageways 28 extend transversely from the liquid feed chamber 26 and open at the outer surface of valve stem 7. As will be appreciated from the more detailed description given below, liquid 5 from within the container 2 passes (during spray discharge) radially inwardly of the liquid feed passageways 28 into chamber 26 and then via passageway 27 into the flow conduit 8. In this way, flow passageway 27 provides a liquid inlet for the flow conduit 8.

Two gas bleed inlet passageways 29 extend transversely from the flow conduit 8 to open at the exterior surface of valve stem 7. The liquid feed passageways 28 and gas bleed inlet passageways 29 are axially spaced from each other by a distance such that, in the "rest" condition of the aerosol as shown in FIG. 1, the passageways 29 are sealed by upper gasket 22 and passageways 28 are sealed by lower gasket 23. The cross-sections of the passageways 28 and 29 together with the axial spacing between these passageways and the dimensions of the upper and lower gaskets 22 and 23 are such that on depression of the valve stem 7 the gas bleed inlet passageways 29 are opened simultaneously with (or more preferably just before) the liquid feed passageways 28. The effect of opening the passageways 28 and 29 will be described more fully below.

Figure 5:
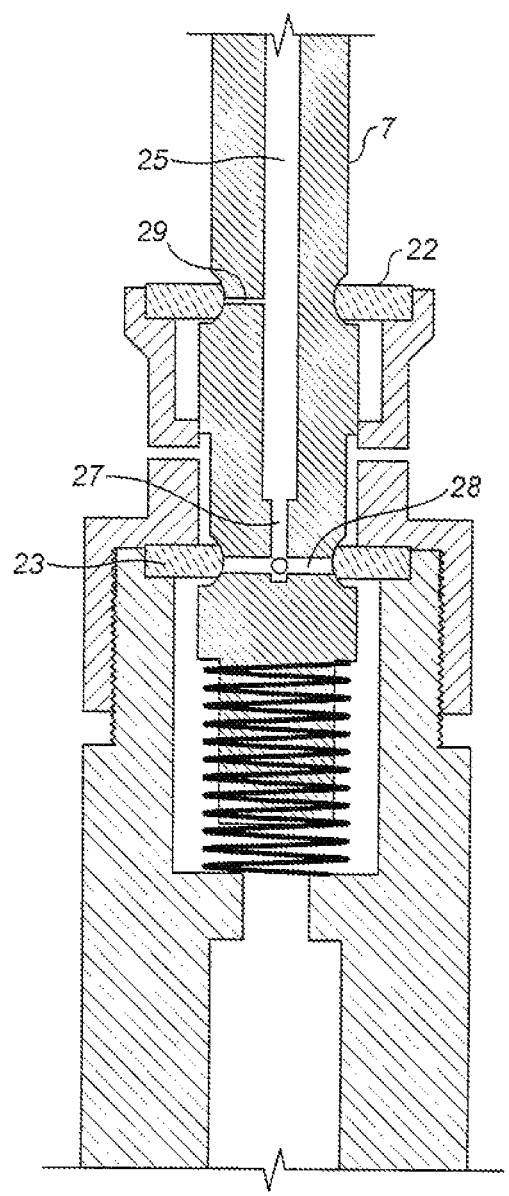
FIG. 5 schematically illustrates a first alternative valving arrangement in accordance with the invention.

It will be appreciated that constructions in which there is only one such liquid feed passageway 28 and/or one gas bleed inlet passageway 29 are also practical. By way of example of the latter alternative arrangement, the embodiment illustrated in FIG. 5 has just a single gas bleed inlet passageway 29. The embodiment of FIG. 5 also omits the chamber 26, the liquid feed passageways 28 extending directly to the passageway 27.

Reference is now made to the spray outlet region 11 of the actuator cap 10. This region 11 is formed internally with an integrally moulded boss 30 arranged such that, on the one hand, it defines an annular clearance or gallery 31 within the actuator cap 10 and, on the other hand, its free end is located a short distance from the exterior of cap 10 to leave a cylindrical gap in which the MBU insert 13 is located. This insert is described in more detail below but, at this point, it will be appreciated that conduit section 12*b* communicates with the annular gap 31 so that fluid being discharged from container 2 may pass circumferentially around this gap.

MBU insert 13 is of conventional construction and is shown in more detail in the insets to FIG. 1. In conventional manner the insert 13 is circular and has a central orifice 32, which on one (upstream) face of the insert 13 is surrounded by a well 33 in communication with channels 34 extending outwardly of well 33. MBU insert 13 has an outer diameter such that it is a tight push fit within the outer end of outlet region 11 so that its upstream face formed with the well 33 and the channels 34 abuts against the free end of boss 30 with the outer ends of channels 34 being in communication with the annular space 31 fed by conduit section 12*b*. It will be appreciated that with the MBU insert 13 located in position as described, the well 33 forms a swirl chamber 35 with the end face of boss 30, the channel 35 being fed via the channels 34.

To operate the device 1, actuator cap 10 is depressed so that valve stem 7 moves downwardly against the bias of spring 14. As a result, gas bleed inlet passageways 29 are displaced from the gasket 22 such that compressed gas can bleed from head space 6 into the flow conduit 8 via the ports 24 (in the wall of housing 9), the annular clearance 21*a* and the gas bleed inlet passageways 29. Simultaneously with, or preferably slightly later than, the creation of the gas flow, one or more of the liquid inlet passageways 28 are opened by virtue of moving past lower gasket 23. Liquid 5 can now flow into liquid feed chamber 26 by passage upwardly along the dip tube 20, through the inlet 16 into the housing 9, into annular clearance 21*b* and through the liquid inlet passageways 28. Liquid 5 introduced into liquid feed chamber 26 passes via passageway 28 into flow conduit 8 where it is mixed with compressed gas bled through the passageways 29. A bubble laden flow of homogeneous bubbles with similar diameters and without significant coalescence or stratification is formed in flow conduit 8 and flows along the conduit 8 into conduit section 12*a* (within actuator cap 10) and then into conduit section 12*b*. From this latter conduit section, the bubble laden flow passes into, and around, the annular gallery 31 and then enters the outer ends of swirl channels 34 before passing into swirl chamber 35 and out through discharge orifice 32.

In the construction of the aerosol spray device 1, it should be ensured that the total cross-sectional area of the gas bleed passageways 29 should not be so large that excessive gas is bled into the conduit 8 such that the container 2 is depleted of pressurised gaseous propellant before all of the liquid 5 in the container has been discharged. Typically, the total cross-sectional area of the gas bleed inlet passageways 29 should be equivalent to that of a singular, circular section inlet with a diameter of 0.15-0.7 mm.

Preferred dimensions for the construction of spray device 1 to ensure production of a bubble laden flow of homogeneous bubbles with similar diameters and without coalescence or stratification are shown in the following table:

| Item | Reference Numeral | Diameter | Length |
|---|---|---|---|
| Gas bleed inlet | 29 | 0.15 mm each (two provided) | 1.0 mm |
| Liquid inlet passageway | 27 | 0.4 mm (one provided) | 1.0 mm |
| Conduit in Valve Stem | 8 | 1 mm | 10 mm |
| Exit Orifice of MBU | 32 | 0.33 mm | |

| Item | Reference Numeral | Diameter | Length |
| --- | --- | --- | --- |
| Well | 33 | 0.75 mm | 0.3 mm (depth) |
| Channels | 34 | 0.2 mm (width) | 0.3 mm (depth) |

With the dimensions as indicated above, the spray device 1 is particularly suitable for consumer aerosol products such as polishes and air fresheners.

Figure 2:
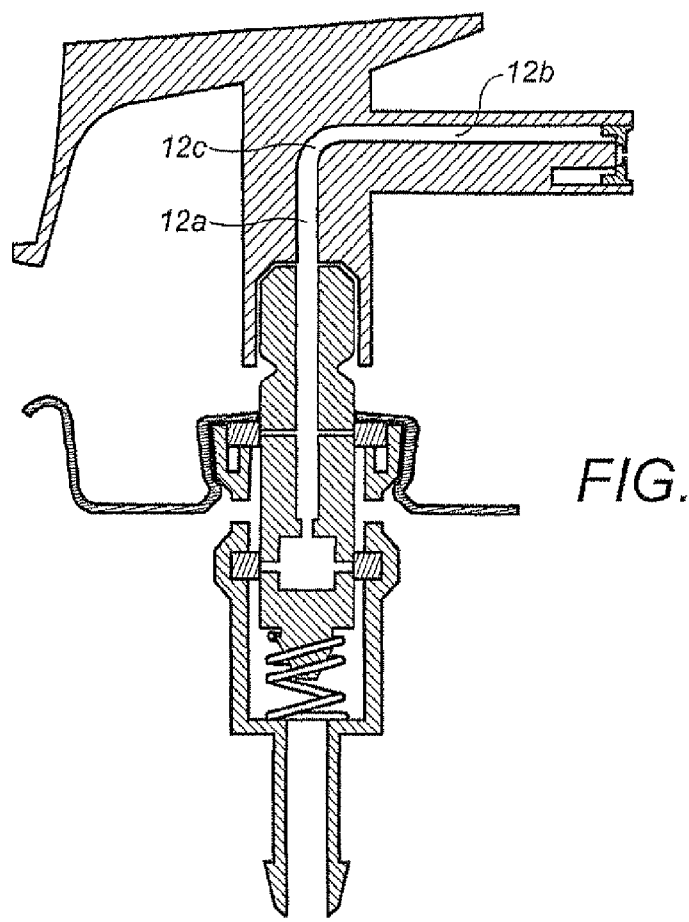
FIG. 2 schematically illustrates a second embodiment of aerosol spray device in accordance with the invention.

The (second) embodiment shown in FIG. 2 of the drawings is similar to that of FIG. 1 but sections 12a and 12b of the discharge conduit in the actuator cap 10 are connected by a curved transition region 12c. This curved transition region 12c ensures that there is less disturbance of the bubble laden flow in its passage from its generation to the outlet region 11 of the actuator cap.

Figure 3:
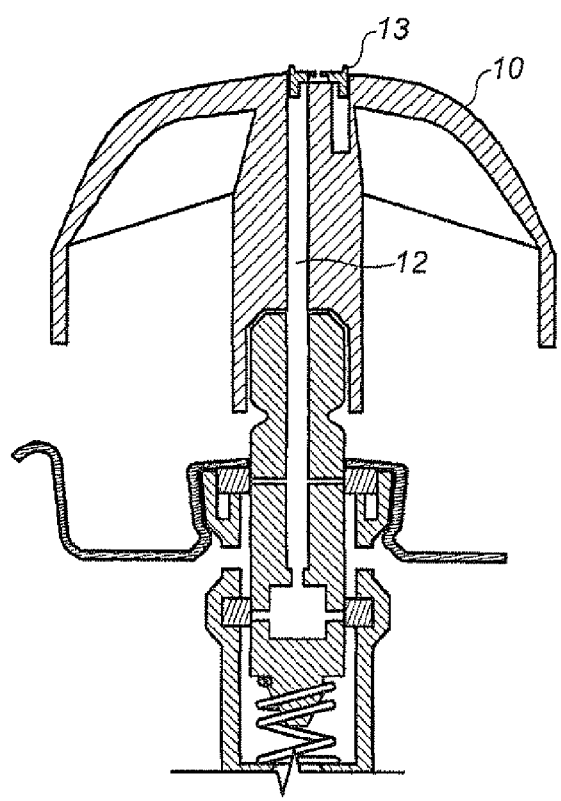
FIG. 3 schematically illustrates a third embodiment of aerosol spray device in accordance with the invention.

Reference is now made to FIG. 3, which shows a third embodiment of aerosol spray device in accordance with the invention. In essence, the embodiment of FIG. 3 is very similar to that of FIG. 1 (and the same reference numerals define like parts) save that the discharge conduit 12 within actuator cap 10 is linear rather than being sub-divided into sections 12a and 12b at right angles to each other, as is the case in the embodiment of FIG. 1. The provision of a linear discharge conduit 12 within actuator cap 10 is advantageous in providing less disturbance to the bubble laden flow and results in a spray device capable of producing steadier and finer sprays than that of the embodiment shown in FIG. 1. The device of FIG. 3 is particularly suitable for air fresheners.

Figure 4:
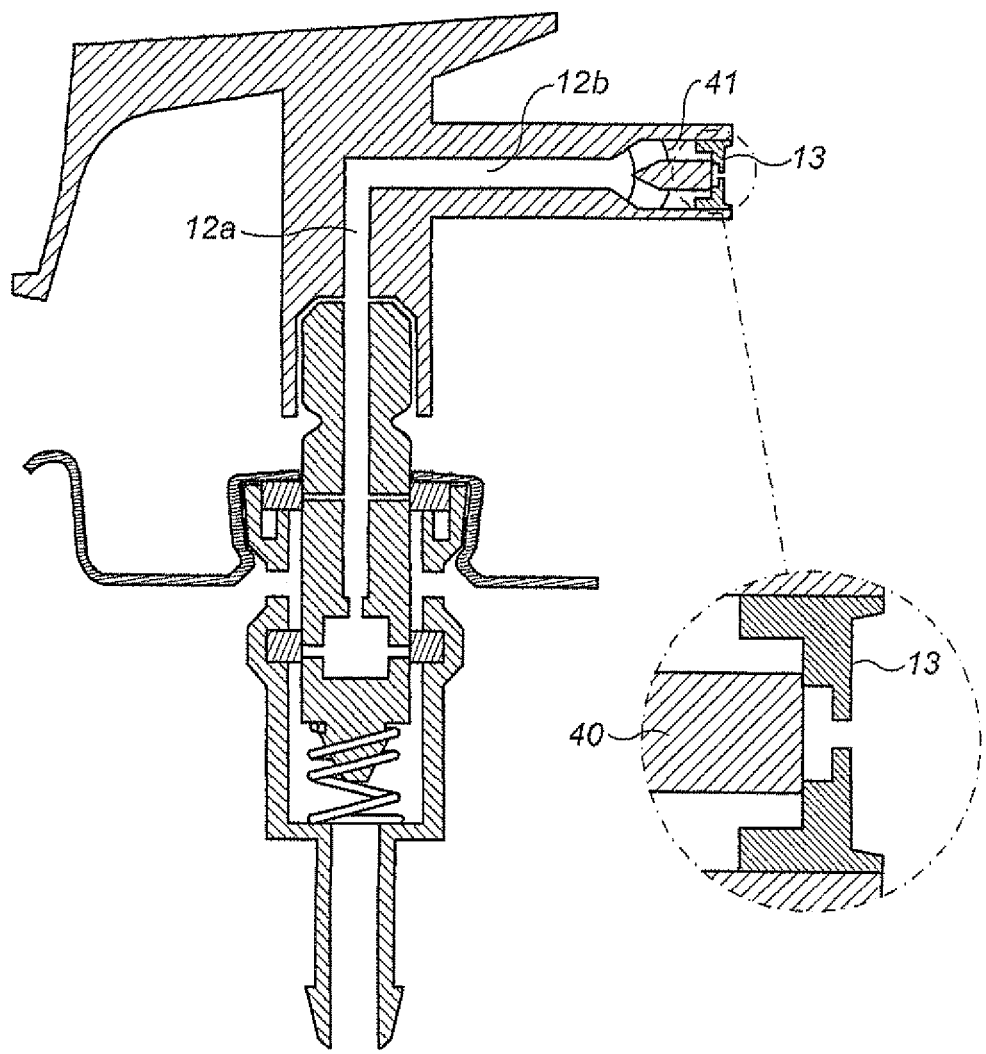
FIG. 4 schematically illustrates a fourth embodiment of aerosol spray device in accordance with the invention.

The (fourth) embodiment shown in FIG. 4 is based on that shown in FIG. 1 (with an abrupt right-angled transition between discharge conduit sections 12a and 12b in actuator cap 10) but differs in the configuration of the outlet region 11. In the embodiment of FIG. 4, outlet section 12b feeds coaxially into the gallery 31 (in contrast to the preceding embodiments, in which the feed into the gallery 31 has been off-centre). In this case, the gallery 31 is provided around an insert 40 supported on struts 41.

Figure 6:
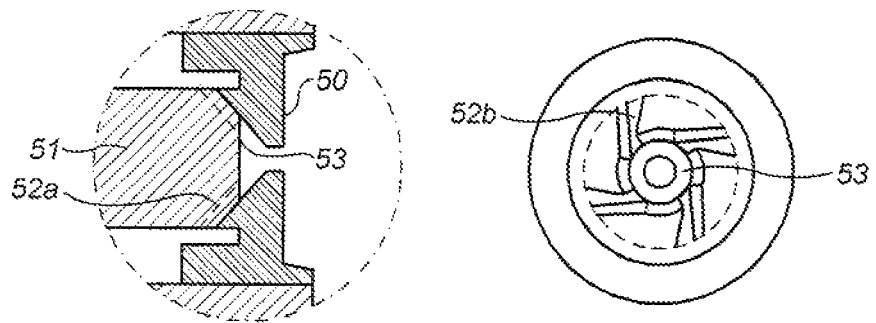
FIG. 6 illustrates a nozzle arrangement that may be employed in aerosol spray devices in accordance with the invention.

As thus far described, the MBU inserts 13 shown in FIGS. 1 to 4 are identical with each other. However various other forms of MBU insert may be employed, for example as depicted for the MBU insert 50 shown in FIG. 6 of the drawings. In this embodiment, the boss 51 has a bevelled peripheral edge and the insert 50 has a conical surface that locates on the bevelled free edge, as clearly depicted in FIG. 6. In this case, the swirl channels may be formed on the bevelled edge of the boss 51 (wherein referenced 52a) or in the insert 50 itself (wherein referenced 52b), or a combination of both. For either possibility, the swirl channels 52a, 52b have components of their directions in the axial direction as well as tangential to the swirl chamber 53.

Figure 7:
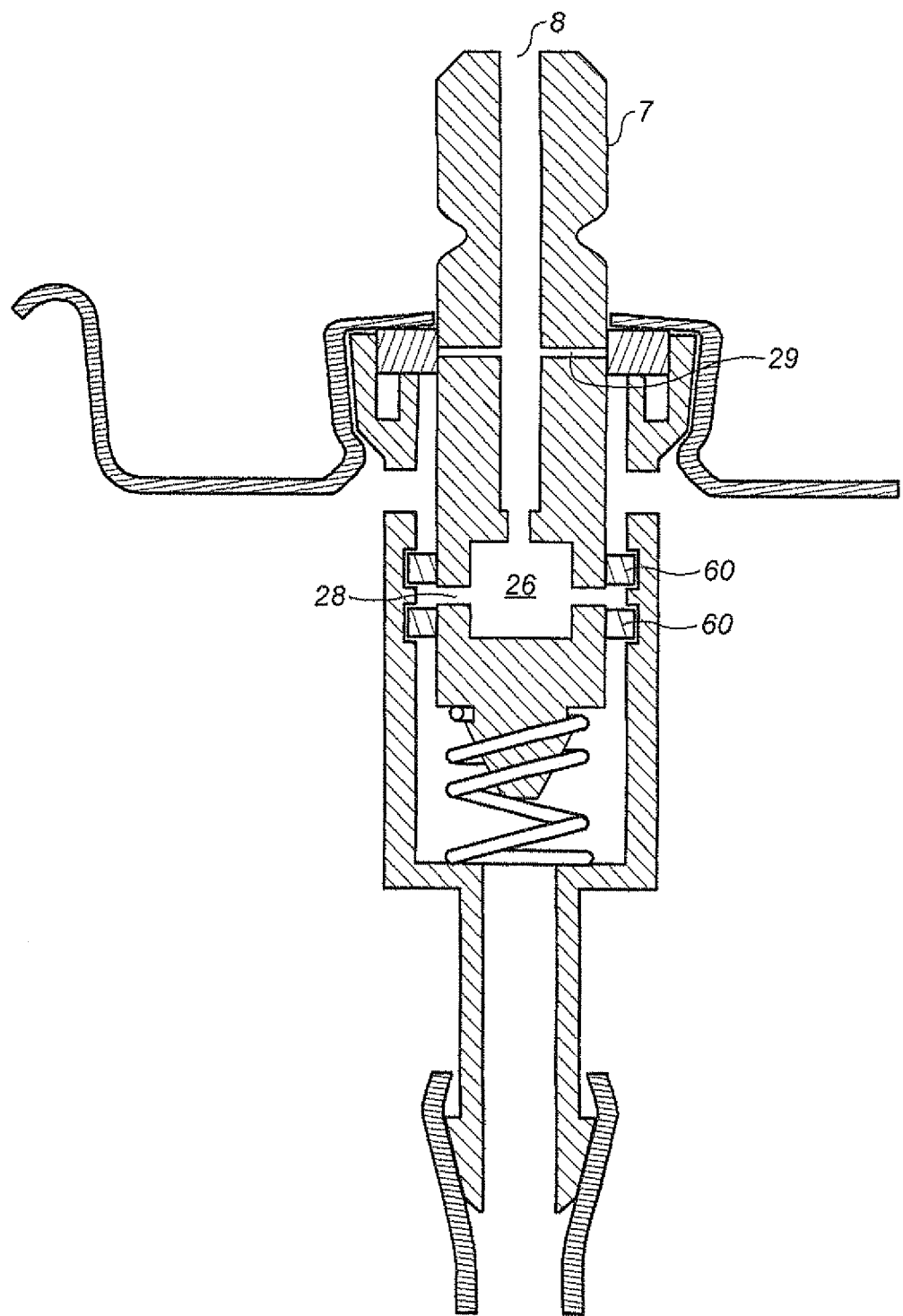
FIG. 7 schematically illustrates a second alternative valving arrangement in accordance with the invention.
Figure 8:
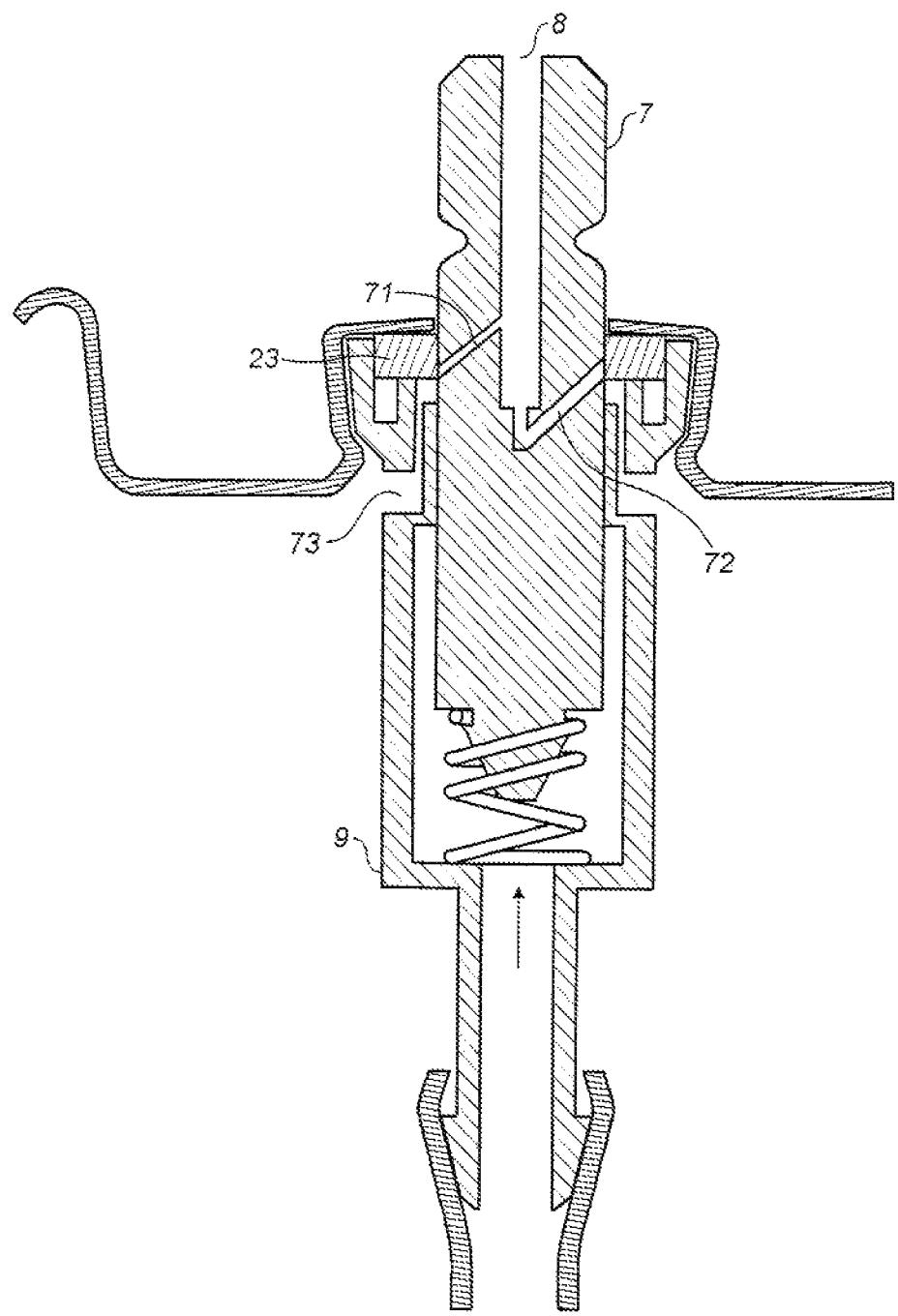
FIG. 8 schematically illustrates a third alternative valving arrangement in accordance with the invention.

FIGS. 7 and 8 of the drawings show modified valving arrangements for producing the bubble-laden flow to be passed to the MBU insert.

The arrangement of FIG. 7 is similar to that of FIG. 1 save that (in the rest condition of the aerosol spray device) the passageways 28 are isolated from the liquid 5 by two O-rings 60, one above each passageway 28 and one below. When valve stem 7 is depressed, the passageways 28 move past the lower O-ring 60 so as to be exposed to the high pressure liquid in the valve housing thus permitting liquid flow into the conduit. The gas bleed inlets 29 function in exactly the same way as outlined above.

It should be noted that, although the embodiments of FIGS. 1 to 5 and 7 show a single liquid inlet passageway 27 entering coaxially into the conduit 8 at the lower end thereof, it is possible for there to be two or more liquid inlets which can be formed in the side wall of the lower part of the conduit. Furthermore although the embodiments of FIGS. 1 to 4 and 7 show the chamber 26 (that feeds the liquid inlet 27 to the conduit 8) being fed with liquid via two passageways 28, it is possible for the valve stem to be modified such that the chamber 26 and liquid inlet 27 are omitted and the flow conduit 8 is fed directly via passageways 28 provided that they are of appropriate cross-section (as, for example, shown in FIG. 5).

In the arrangement of FIG. 8, the lower seal 23 has been omitted and modifications made to the valve stem 7 and the housing 9 to permit the arrangement to function with the remaining, single seal 23. More specifically, the valve stem 7 incorporates for the conduit 8, a gas bleed inlet 71 and a liquid inlet 72 which, in principle, perform the same functions as passageways 29 and 28 respectively in the arrangement of FIG. 1. As shown in FIG. 8 for the rest condition of the aerosol spray device, gas bleed inlet(s) 71 is closed by seal 23 and extends upwardly away therefrom. Liquid inlet(s) 72 is of angled configuration with a short section coaxial with conduit 8 connected to a further section extending upwardly to seal 23 so as to be closed by that seal. Alternatively, inlet(s) 72 may enter directly into the side of the conduit 8. In other embodiments, the second inlet(s) 71 may be perpendicular to the conduit 8 and in a further embodiment both the first and second inlets, 72 and 71, may enter the conduit 8 at the same orthogonal plane as the conduit 8. Additionally, a portion of the housing 9 has been modified so as to be a close sliding fit around that region of the valve stem 7 where the gas bleed inlet 71 opens at the outer surface of valve stem 7. Furthermore gas feed port 73 (equivalent to port 24 in FIG. 1) has been configured so that its outlet end feeds directly into gas bleed inlet 71 when valve stem 7 is depressed. These arrangements avoid leakage of gas from the headspace of the container into the liquid inlet 72 or liquid leaking into the gas inlet 71. Whilst it is desirable to avoid such leakages as much as possible they are not a major problem because the gas and liquid are at essentially the same pressure in the container 2.

The embodiment of FIG. 8 has various advantages as compared to that shown in, and described with reference to, FIG. 1. In particular, it employs fewer parts and thus reduces material, manufacturing and assembly costs. Additionally it may readily be produced in dimensions well suited to manufacture with the same overall dimensions as conventional liquefied gas propellant aerosol valves.

Further alternative embodiments are illustrated in FIGS. 9a to 16, in all of which the gasket 22 is omitted.

Figure 9A:
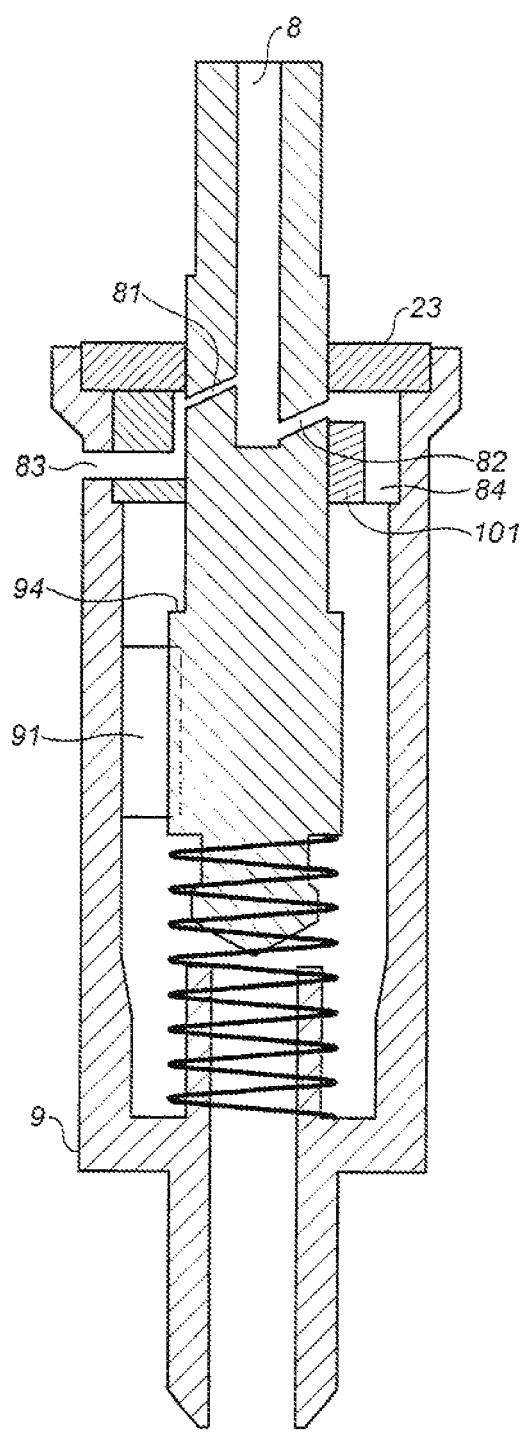
FIGS. 9a and 9b schematically illustrate a fourth alternative valving arrangement in accordance with the invention in respective open and rest conditions.
Figure 9B:
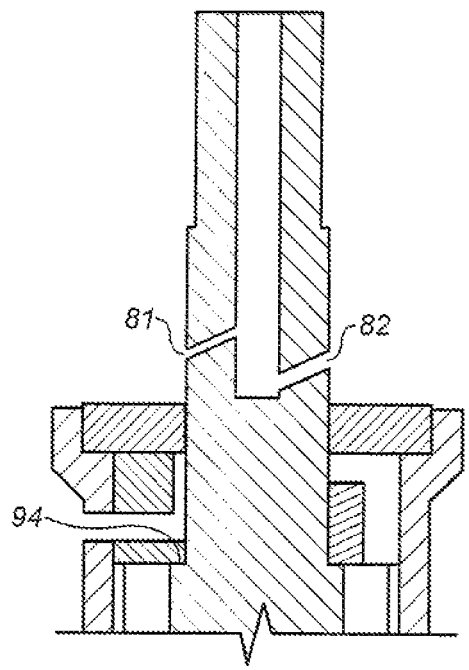
Figure 10:
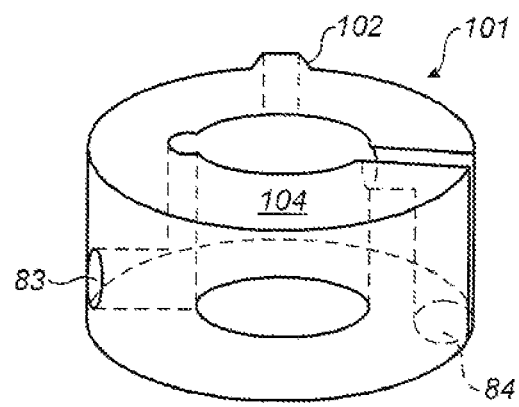
FIG. 10 is a perspective view of a distributor plug as used in the valving arrangement of FIGS. 9a and 9b, showing internal conduits.
Figure 11:
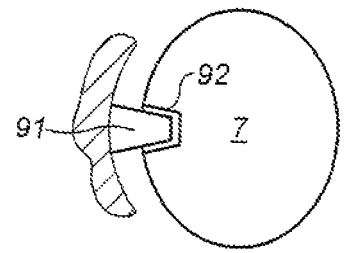

FIGS. 9a and 9b show, in respective open and rest conditions, such an alternative 'single gasket' embodiment in which a modified housing 9 contains a distributor plug 101 at its upper end. The distributor plug is a generally annular piece having a chamber 104 defined by an interior surface thereof. The plug has a locator lug 102 projecting from an outer surface for cooperative engagement with a mating recess (not shown) in the interior wall of the housing 9 to ensure proper orientation of the plug 101 within the housing 9. An L-shaped gas inlet channel 83 extends from the headspace to the chamber 104. An inverted L-shaped fluid inlet channel 84 extends from the fluid-filled interior of the housing 9 to the chamber 104 at a position opposite to the gas channel 83. The plug 101 may be formed of acetal or other suitable hard plastic material. Alternatively, it may comprise moulded rubber. The plug may be injection moulded, in which case it may be formed integrally with the seal 23. In one embodiment, the plug may be provided with an additional lip seal (not shown) surrounding the bottom edge of the chamber 104 to improve sealing and ensure no leakage of liquid into the gas flow path.

As with the embodiment of FIG. 8, in the embodiment of FIGS. 9a to 11, modifications have been made to the valve stem 7 and the housing 9 to permit the arrangement to function with the remaining, single seal 23. More specifically, the valve stem 7 incorporates for the conduit 8, a gas bleed inlet 81 and a liquid inlet 82 which, in principle, perform the same functions as passageways 29 and 28 respectively in the arrangement of FIG. 1. As shown in FIG. 9b for the rest condition of the aerosol spray device, the valve stem 7 is extended out of the housing 9, under the action of the spring 14, so that the gas bleed inlet(s) 81 and the liquid inlets(s) are each on the opposite side of the seal 23 to the distributor plug 101 and therefore not in communication, respectively, with the headspace and the interior of the housing 9.

The gas bleed inlet 81 is similar to that (71) of the embodiment of FIG. 8. The liquid inlet(s) 82 is, like that (72) of the embodiment of FIG. 8, of angled configuration, but in this instance is not joined with a short section coaxial with the conduit 8. Instead, the inlet(s) 82 enters directly into the side of the conduit 8. As with FIG. 8, in other embodiments, the second inlet(s) 81 may be perpendicular to the conduit 8 and in a further embodiment both the first and second inlets, 82 and 81, may enter the conduit 8 at the same orthogonal plane as the conduit 8.

The chamber 104 is dimensioned so as to be a close sliding fit around that region of the valve stem 7 where the gas bleed inlet 81 and the liquid feed inlet 82 open at the outer surface of valve stem 7. As a result of the close sliding fit, no liquid can leak past the valve stem/chamber interface and so the gas flow path will not be contaminated with any liquid from the chamber, which leakage could impede the performance of the spray aerosol.

When the valve stem 7 is depressed, the gas bleed inlet 81 and the liquid feed inlet 82 are pushed past the gasket 23 and into communication with the respective gas channel 83 and fluid inlet channel 84.

In order to prevent rotation of the valve stem 7 within the housing 9, the housing may include a projection 91 for cooperative engagement with a corresponding recess 92 in the valve stem. To prevent the valve stem 7 from extending too far out of the housing 9, a lower portion of the stem may be enlarged, defining a step 94 that acts, in conjunction with the underside of the distributor plug 101, as a limit stop (see FIG. 9b).

Another alternative embodiment is illustrated in FIGS. 12a to 14. Transverse gas bleed inlet 121 replaces the angled gas bleed inlet 81 of the preceding embodiment; angled liquid feed inlet 122 replaces the similar inlet 82 (although joining the conduit 8 slightly higher up).

Instead of a projection from the housing cooperating with a recess on the valve stem to prevent relative rotation of those parts, in this embodiment lugs 7a project from the valve stem 7 and are received in grooves 9a in the interior of the housing 9 and extending parallel to the axis thereof. The liquid inlet arrangement is also different, in that an axial channel 106 through the lower portion of the valve stem 7 extends to be in fluid communication with the aperture 16 in the lower wall of the housing 9. A transverse opening 108 is located at the upper end of the channel 106 and connects the channel 106 to the annular clearance 21 between the stem 7 and the housing 9.

At the upper end of the housing, the distributor plug 101 of FIGS. 9a to 11 is replaced by an annular bush 110 and a thin gasket 112 sandwiched between the upper end of the bush and the seal 23. The thin gasket 112 is shown in greater detail in FIG. 14 and comprises a disc having a central aperture 113 that is sized to be a close fit about the valve stem. A radial groove 123a extends in one side of the disc from the central aperture to an edge of the disc, where the groove connects with an axial notch 123b that extends through the edge of the disc. The groove 123a and notch 123b together comprise a gas inlet port that forms a gas flow path from the headspace to the gas bleed inlet 121 when the valve stem is depressed, as in FIG. 12a. A notch 124 extends through the disc 112 at a point at the edge of the aperture 113 diametrically opposite to the groove 123a. When the valve stem is depressed, the notch 124 forms a liquid flow path between the annular clearance 21 and the liquid feed inlet 122.

Figure 12A:
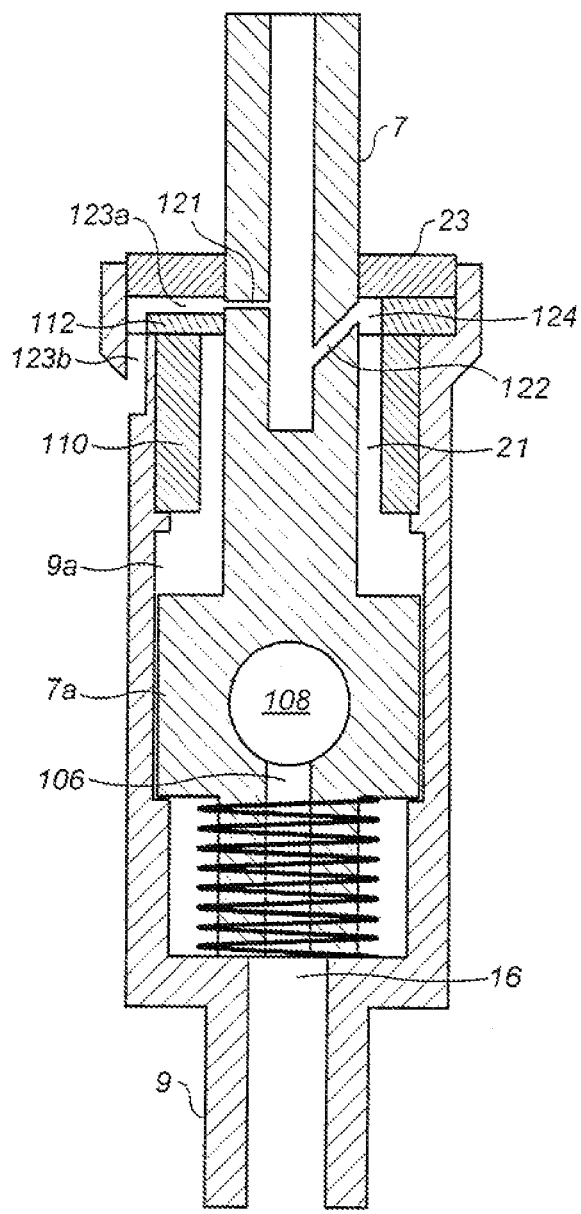
FIGS. 12a and 12b schematically illustrate a fifth alternative valving arrangement in accordance with the invention in respective open and rest conditions.
Figure 12B:
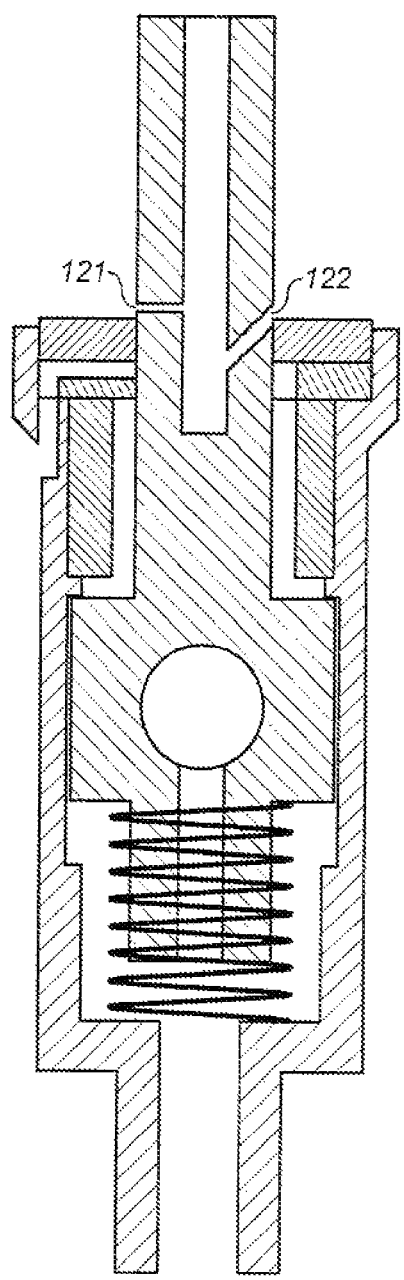
Figure 13:
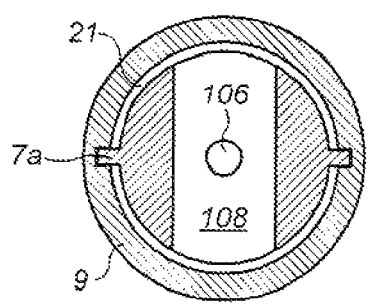
Figure 14:
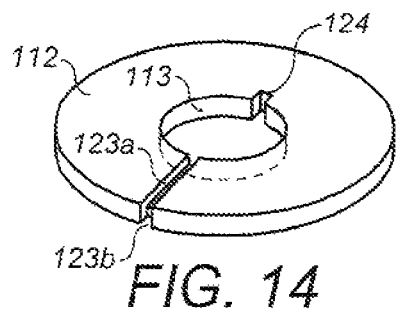
FIG. 14 is a perspective view of a thin gasket as used in the valving arrangement of FIGS. 12a and 12b.

FIG. 12b shows the valve stem of this embodiment in a rest condition, in which the valve stem 7 is extended out of the housing 9, under the action of the spring 14, so that the gas bleed inlet(s) 121 and the liquid inlets(s) 122 are each on the opposite side of the seal 23 to the gasket 112, or are at least blocked by the seal. The bush 110, in conjunction with an enlarged portion of the valve stem 7, may also act as a limit stop to prevent over extension of the stem out of the housing 9.

Figure 15:
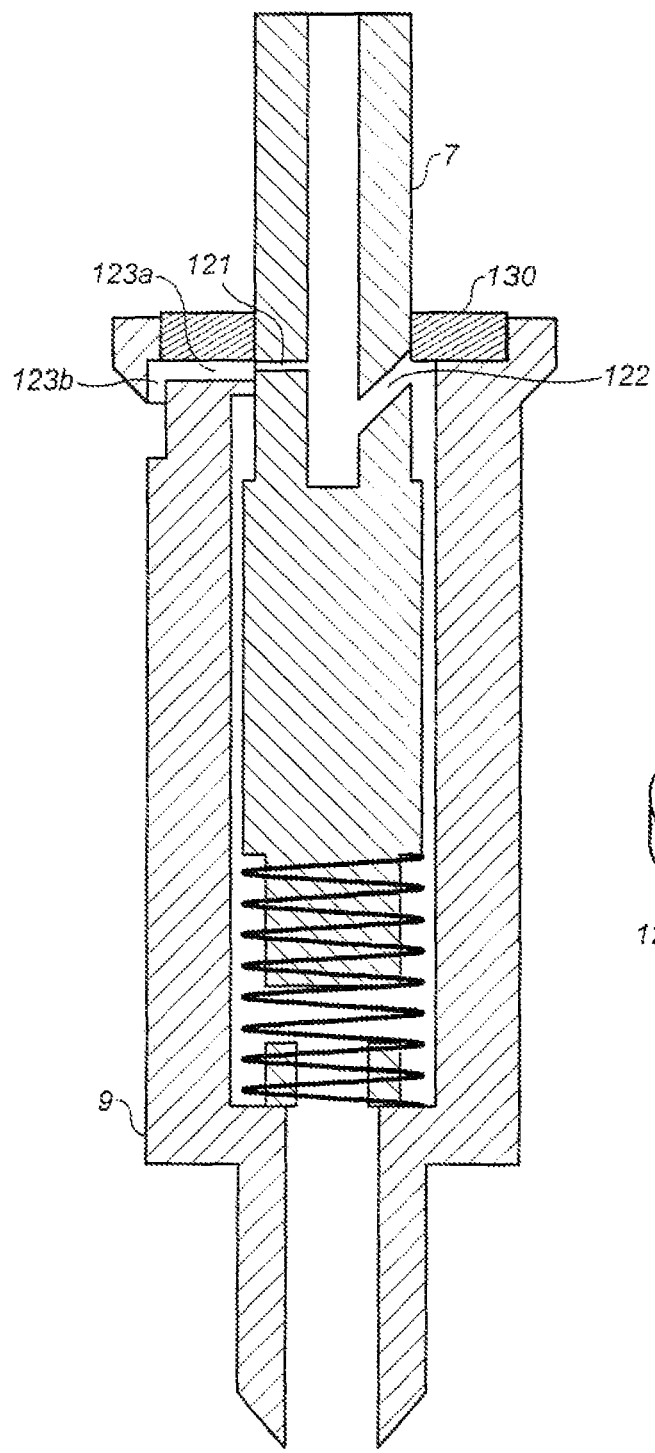
FIG. 15 schematically illustrates a sixth alternative valving arrangement in accordance with the invention.
Figure 16:
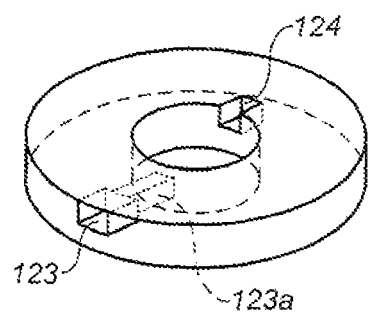
FIG. 16 is a perspective view from below of a thick gasket as used in the sixth alternative valving arrangement of FIG. 15.

FIGS. 15 and 16 are schematic illustrations of an alternative embodiment. Rather than having separate seal 23 and thin gasket 112, a single, thick gasket 130 is used. This could be manufactured using injection moulding techniques, for example, to incorporate the respective gas and liquid flow passages 123a,b; 124.

It should be appreciated that various modifications may be made to the illustrated embodiments. Thus, for example, the spray devices shown in FIGS. 1-4 and 6 may have a single gas bleed inlet 29 (see FIG. 5) and/or a single liquid feed inlet 28 or may have three or more such inlets. Similarly the embodiment of spray device shown in FIG. 7 may have two or more of each of the gas bleed inlet 29 and liquid feed inlet 28. In general, aspects of the various different embodiments may be combined such that, for example, any of the valve stem configurations may be combined with any of the cap configurations and likewise either may be combined with any of the alternative outlet region configurations. More generally, embodiments of spray device in accordance with the invention may have 1 to 6 gas bleed inlets, preferably with a total cross-section equivalent to a single inlet of 0.15-0.7 mm diameter. Similarly there may be 1 to 6 liquid inlets with a total cross-section equivalent to a single inlet of 0.15-0.7 mm diameter. Also, rather than having cooperating projection/recess or groove arrangements to prevent relative rotation of the valve stem 7 within the housing 9, due to their round shapes, the stem and the housing could instead have other cross-sectional profiles (such as square) that would inherently prevent such relative rotation.

Furthermore although all embodiments are illustrated with an MBU insert with four swirl channels, it is possible more generally to use inserts with 1 to 8 such channels.

It should be appreciated that the flow conduit/valving arrangements shown in, and described with reference to, FIGS. 7 to 16 above may be employed in the aerosol spray devices which are the subject of, and disclosed in, the aforementioned U.S. patent application.

The following non-limiting Example illustrates the invention.

EXAMPLE

This Example was carried out using an aerosol spray device in accordance with the invention having a discharge assembly with a flow conduit, diameter 1.0 mm and length in the stem 15.0 mm, having a single liquid inlet having a diameter of 0.40 mm and downstream thereof a single gas inlet having a diameter of 0.20 mm. Both diameters are as measured at the point of entry of the inlet into the flow conduit. The liquid and gas inlets are separated by 2.4 mm The aerosol spray device was fitted with an "AQUA" MBU insert having a 0.23 mm exit orifice and the general arrangement was similar to that shown in FIG. 1

The canister of the device had an interior volume of 486 ml which was 50% filled with deionised water. The canister was pressurised to an internal pressure of 12.13 bar using an electrical transducer type of manometer having an accuracy better than 0.01 bar (1.0 kPa).

The valve stem was depressed for successive, discrete periods of 20 seconds until the container was empty. For each discharge, the can pressure was measured and recorded. Additionally for each discharge the spray was collected and weighed (although as an alternative the can could be weighed before and after the discharge, the difference giving the mass of liquid spray, making the reasonable assumption that the mass of gas discharged is negligible).

The mass measurements were used to calculate volume of liquid sprayed (dVL) during spray discharge.

Values for the volume of atomising gas released (dVat ml) were determined by standard equations making use of the ideal gas law relating pressure, volume, mass and temperature of gas so that the mass of gas in the canister is calculated before and after the 20 s spraying interval. In this respect, the product GAS pressure (Abs)×Gas Volume (in can) is proportional to the Mass of Gas left in the can (according to the Gas Law, assuming a constant temperature which is the case for these experiments). This does not need to be used explicitly because the initial volume and pressure of the gas in the can and thus the gas density and thus the initial gas mass in the can are known. The gas density after 20 s can be calculated using the new can pressure and multiplying by the volume of gas in the can (which has increased by a known volume that is equal to the measured volume of liquid sprayed in 20 s) to give the mass of gas left in the can. The difference between the mass of gas in the can before and after the 20 s is the mass of gas that has left the gas.

The average liquid and gas flow rates during the time interval (QL ml/min and Qg ml/min respectively) were simply calculated by dividing the time interval into the volumes of liquid and gas passing through the MBU in that time. Finally the ratio of Qg/QL were determined.

The results are shown in the following Table.

| Discharge No. | initial pressure bar g | final pressure bar g | time interval dt sec | liquid vol sprayed dVL | total discharge time sec | vol atom- izing gas dVat ml | initial liquid in can ml | final liquid in can ml | liquid flow rate QL ml/min | atom gas flow rate Qg ml/min | ratio Qg/QL |
|---|---|---|---|---|---|---|---|---|---|---|---|
| 1 | 12.13 | 10.56 | 20 | 16.3 | 20 | 193.07 | 243 | 226.7 | 48.90 | 579.20 | 11.84 |
| 2 | 10.56 | 9.27 | 20 | 13.9 | 40 | 193.10 | 226.7 | 212.8 | 41.70 | 579.29 | 13.89 |
| 3 | 9.27 | 8.23 | 20 | 14.2 | 60 | 153.12 | 212.8 | 198.6 | 42.60 | 459.36 | 10.78 |
| 4 | 8.23 | 7.32 | 20 | 13.7 | 80 | 147.30 | 198.6 | 184.9 | 41.10 | 441.91 | 10.75 |
| 5 | 7.32 | 6.58 | 20 | 12.7 | 100 | 126.59 | 184.9 | 172.2 | 38.10 | 379.76 | 9.97 |
| 6 | 6.58 | 5.96 | 20 | 12.0 | 120 | 109.44 | 172.2 | 160.2 | 36.00 | 328.33 | 9.12 |
| 7 | 5.96 | 5.39 | 20 | 10.9 | 140 | 117.38 | 160.2 | 149.3 | 32.70 | 352.14 | 10.77 |
| 8 | 5.39 | 4.90 | 20 | 10.8 | 160 | 102.33 | 149.3 | 138.5 | 32.40 | 306.98 | 9.47 |
| 9 | 4.90 | 4.46 | 20 | 10.3 | 180 | 94.21 | 138.5 | 128.2 | 30.90 | 282.63 | 9.15 |
| 10 | 4.46 | 4.09 | 20 | 10.0 | 200 | 83.31 | 128.2 | 118.2 | 30.00 | 249.92 | 8.33 |
| 11 | 4.09 | 3.74 | 20 | 9.6 | 220 | 80.61 | 118.2 | 108.6 | 28.80 | 241.84 | 8.40 |
| 12 | 3.74 | 3.42 | 20 | 8.6 | 240 | 86.20 | 108.6 | 100 | 25.80 | 258.59 | 10.02 |
| 13 | 3.42 | 3.14 | 20 | 8.4 | 260 | 70.98 | 100 | 91.6 | 25.20 | 212.94 | 8.45 |
| 14 | 3.14 | 2.83 | 20 | 8.3 | 280 | 90.47 | 91.6 | 83.3 | 24.90 | 271.40 | 10.90 |
| 15 | 2.83 | 2.58 | 20 | 8.3 | 300 | 70.54 | 83.3 | 75 | 24.90 | 211.63 | 8.50 |
| 16 | 2.58 | 2.39 | 20 | 7.3 | 320 | 55.84 | 75 | 67.7 | 21.90 | 167.51 | 7.65 |
| 17 | 2.39 | 2.19 | 20 | 7.2 | 340 | 58.59 | 67.7 | 60.5 | 21.60 | 175.78 | 8.14 |
| 18 | 2.19 | 2.03 | 20 | 6.6 | 360 | 47.21 | 60.5 | 53.9 | 19.80 | 141.63 | 7.15 |
| 19 | 2.03 | 1.86 | 20 | 6.5 | 380 | 54.85 | 53.9 | 47.4 | 19.50 | 164.54 | 8.44 |
| 20 | 1.86 | 1.72 | 20 | 6.4 | 400 | 46.20 | 47.4 | 41 | 19.20 | 138.61 | 7.22 |

It can be seen from the Table that the Gas/Liquid volume ratio (final column) is between 8 and 11 for most of the lifetime of the aerosol canister, which represents a very satisfactory result.

For a given exit orifice size the dependency of gas and liquid flow rates on gas and liquid inlet diameters is complex; for example it is proposed that reducing the liquid inlet diameter produces a lowering of pressure inside the conduit which increases the inflow of gas into the conduit. However this increased gas inflow increase the blockage of the bubbly flow at the swirl inlets and exit orifice of the MBU which produces a lowering of the liquid inflow rate from the value expected. In order to take into account these complex effects the inventors carried out testing of valves with different gas and liquid inlet diameters and exit orifice diameters. These are carried out as a function of pressure as a canister empties during spraying. In order to compare the performances using different orifices it is found to be necessary to compare flow rates at different representative pressures and the second table shows this comparison for a range of valve geometries and for two MBU's (exit orifices 0.23 mm and 0.33 mm) for the pressure 9.5 bar. It is noted that when there is more than one liquid inlets it is the "equivalent area" inlet diameter that should be specified for comparison purposes, i.e. the diameter of a single orifice that would have the same cross sectional area as the sum of the cross sectional areas of all of the liquid inlets.

| Number of Liq Inlets | Dliq (equiv) mm | Dgas mm | Dexit 0.23 mm Qliq ml/min | Qg ml/min | Qgas/Qliq | Dexit 0.33 mm Qliq ml/min | Qg mL/min | Qgas/Qliq |
|---|---|---|---|---|---|---|---|---|
| 1 | 0.3 | 0.2 | 23 | 1200 | 52 | 39 | 2200 | 56 |
| 1 | 0.3 | 0.2 | 35.7 | 390 | 10.9 | 65 | 1200 | 18.4 |
| 1 | 0.35 | 0.2 | 29.5 | 700 | 23.7 | 65 | 1300 | 20 |
| 1 | 0.4 | 0.15 | 33.3 | 130 | 3.9 | 116 | 97 | 0.8 |
| 1 | 0.4 | 0.2 | 42 | 579 | 13.8 | | | |
| 2 | 0.42 | 0.25 | 54 | 170 | 3.1 | 79 | 320 | 4 |
| 2 | 0.42 | 0.35 | 19 | 1500 | 78 | 50 | 2400 | 48 |
| 1 | 0.45 | 0.2 | 35 | 820 | 23 | 82 | 1110 | 13.5 |
| 1 | 0.5 | 0.2 | 37.5 | 510 | 13.6 | 103 | 700 | 6.8 |
| 2 | 0.57 | 0.35 | 27 | 1100 | 40 | 59 | 1800 | 30.5 |
| 2 | 0.71 | 0.35 | 35 | 660 | 18.8 | 82 | 1450 | 17.7 |
| 2 | 0.42 | 0.25 | 42 | 270 | 6.4 | 82 | 560 | 6.8 |
| 1 | 0.4 | 0.2 | 37 | 510 | 13.7 | 76 | 1050 | 13.8 |
| 1 | 0.42 | 0.2 | | | | 68 | 1500 | 22 |

Figure 17:
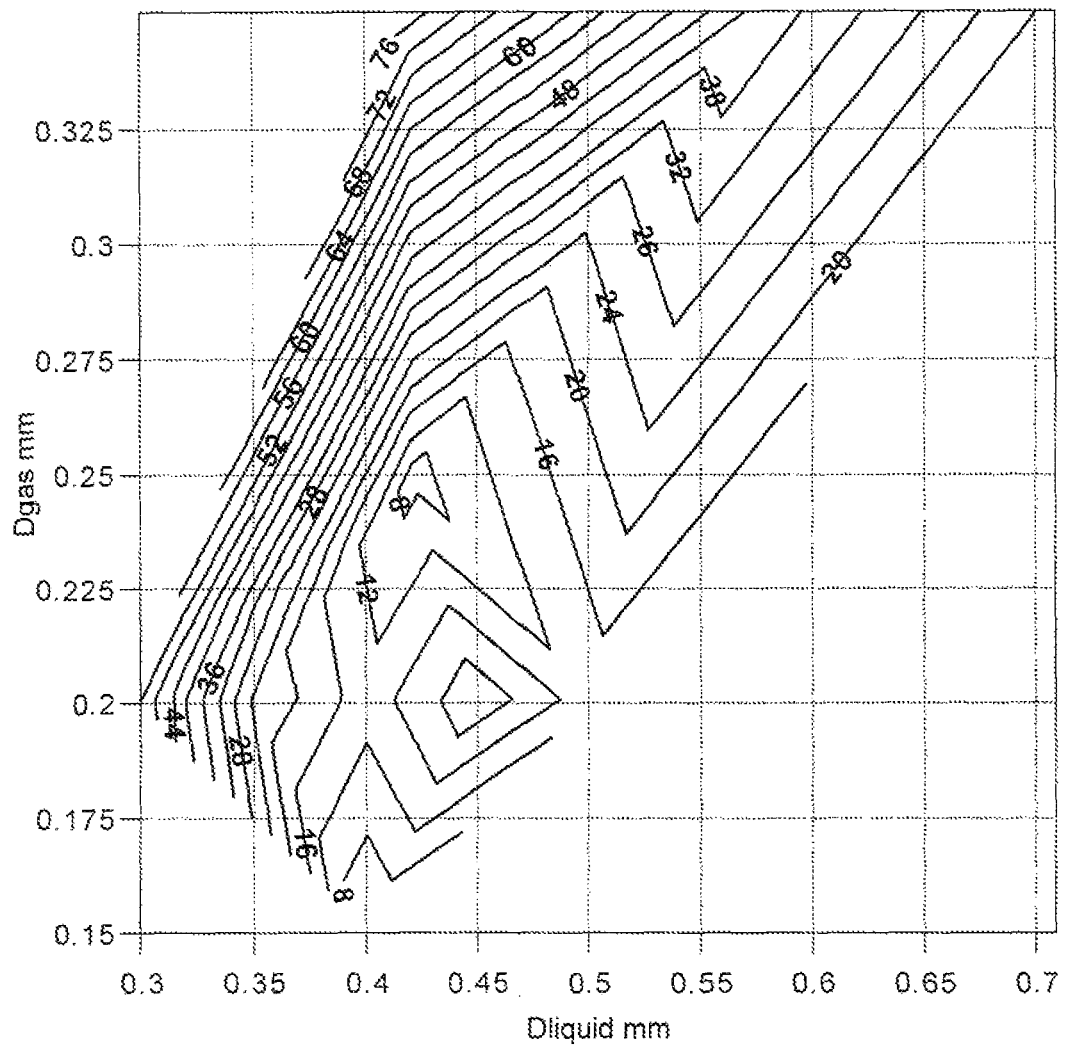
FIGS. 17-20 illustrate the results of the Example below.
Figure 18:
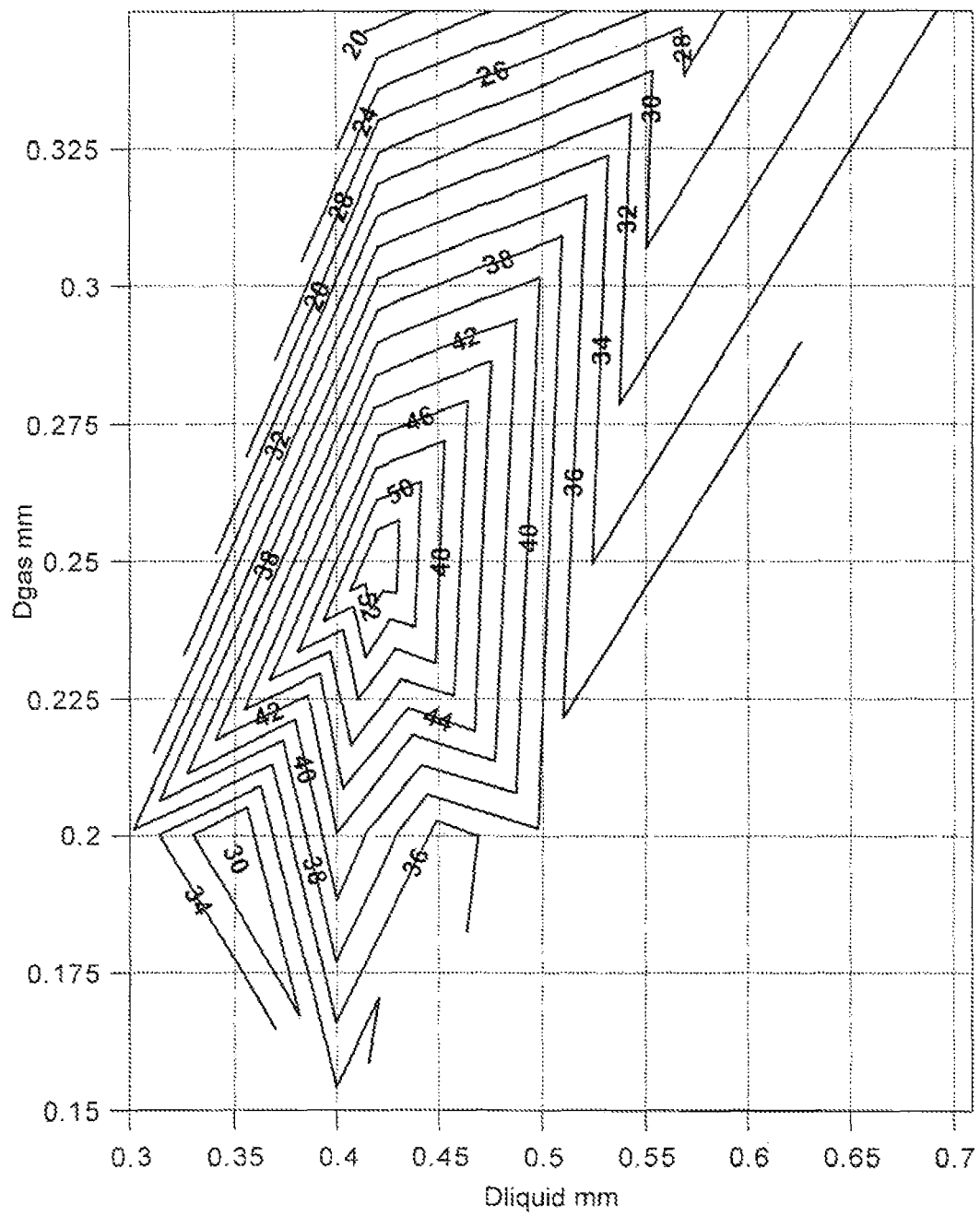
Figure 19:
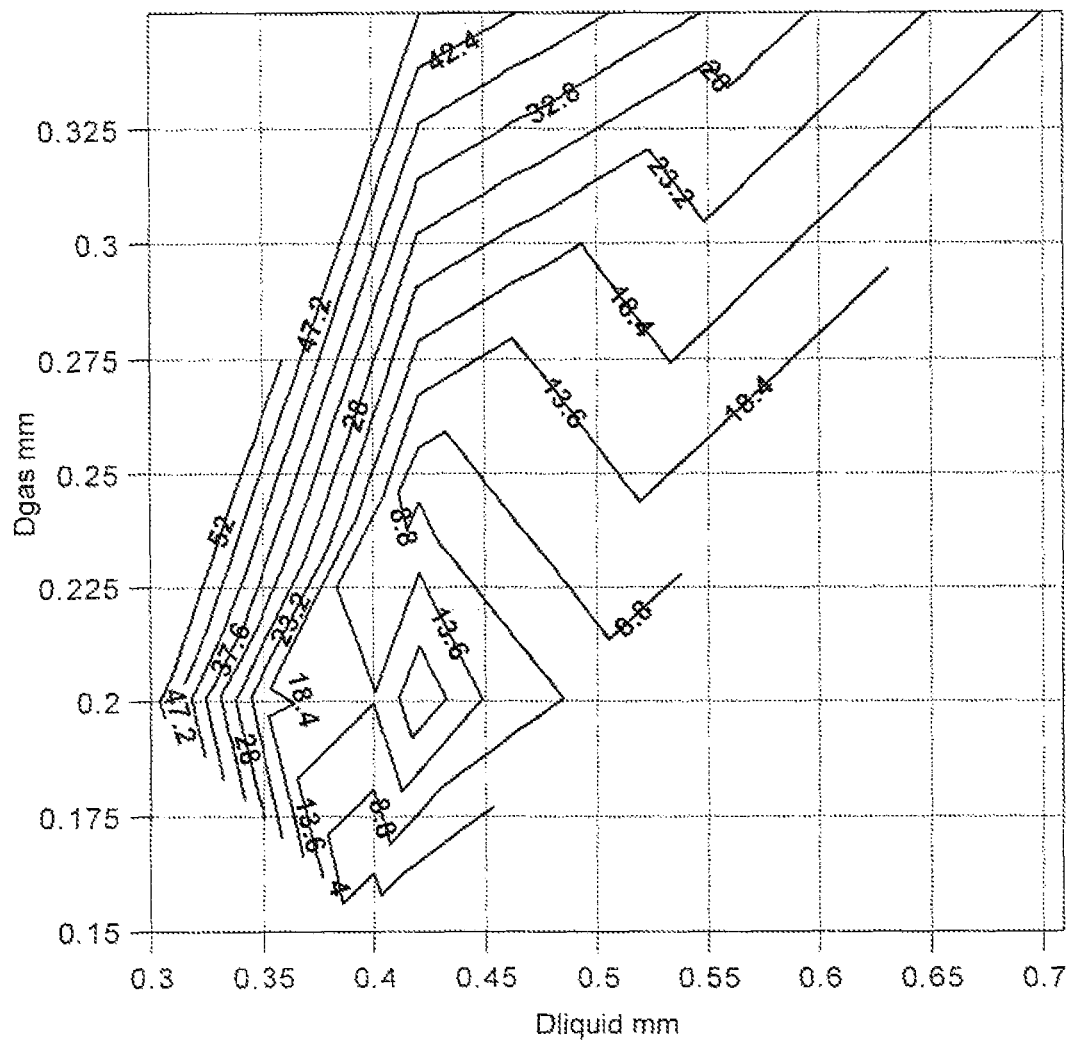
Figure 20:
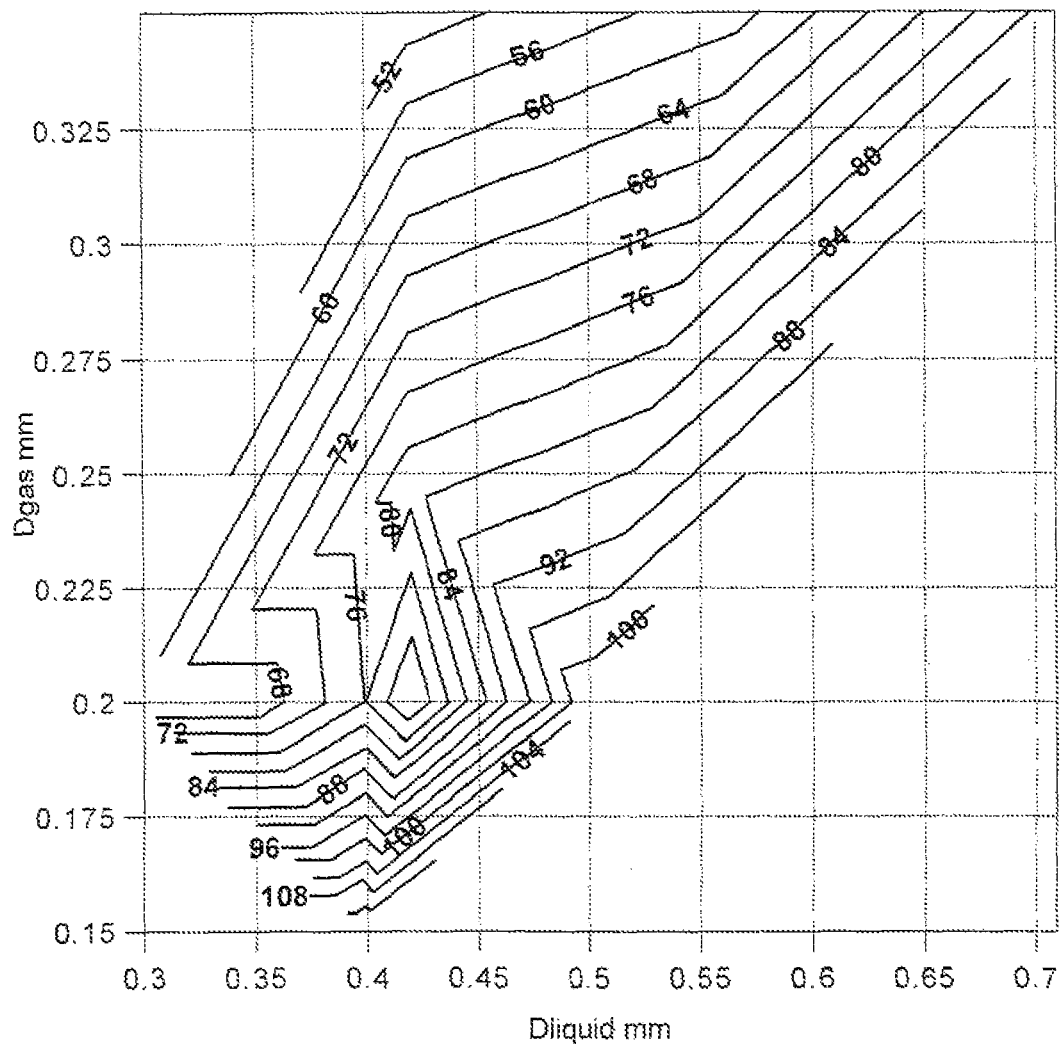

The performance information of the type in the second table is best interpreted by using "iso-contour" 3-dimensional surface plot charts and four examples of these are shown in the four FIGS. 17-20. For instance the first FIG. 17 shows the iso-contours of gas/liquid volume ratio for the 0.23 mm diameter MBU, obtained using software supplied by "DPlot" that takes data in tabular form and constructs contours by interpolation algorithms. In this first FIG. 17 it is seen that there are combinations of values of gas and liquid orifices that are possible to give desirable gas/liquid volume ratios within the bounds of the contour value "16" in the lower central part of the Figure. The second FIG. 18 shows the same 0.23 mm exit case at 9.5 bar but showing iso-contours of the liquid flow rate. From these two figures one may specify combinations of gas and liquid orifice for supplying the highest allowed gas/liquid volume ratio and at a desired flow rate. The same procedure should be carried out at a lower pressure, say 4 bar, in order to ensure that gas/liquid volume ratio and liquid flow rate are acceptable when the canister is nearing the empty state.

Furthermore the procedure should be carried out for more than one value of exit orifice diameter; for example the data for the 0.23 mm orifice case shows flow rates that are too low for air-freshener consumer products and this requires optimising the gas and liquid inlets using a larger exit orifice diameter. The third and fourth Figures: 19 and 20 respectively, show the iso-contours of gas/liquid volume ratio and liquid flow rate for the case of a 0.33 mm exit orifice and it is found that optimisation is achieved at approximately 75% higher liquid flow rates than for the 0.23 mm case.

To minimise the droplet sizes it is necessary to maximise the gas/liquid volume ratio however smaller exit orifices and higher canister pressures also reduce drop size.

The invention claimed is:

1. A valving arrangement for an aerosol spray device comprising a pressurised or pressurisable container holding a liquid to be discharged from the device by a propellant, the valving arrangement comprising:

a valve stem moveable from a first limit position to a second limit position to effect spray discharge from the device;

a flow conduit for supplying fluid from the container to a spray outlet region, said flow conduit being provided in said valve stem and having at least one first liquid inlet for liquid from the container and at least one second gas inlet at the same distance along said flow conduit as said first liquid inlet(s) or downstream of said first liquid inlet(s) for propellant gas from a headspace of the container, wherein each of said first liquid inlet(s) and said second gas inlet(s) is provided in said valve stem; and a seal, formed from an upper gasket and a lower gasket, wherein the upper gasket is configured to close both the first liquid inlet(s) and the second gas inlet(s) when the valve stem is in its first limit position;

wherein movement of the valve stem from its first to its second limit position opens said first liquid inlet(s) and said second gas inlet(s) to respectively cause gas and liquid to be introduced separately into the flow conduit to thereby cause a bubble laden flow to be created therein and movement of the valve stem back to its first limit position closes said first liquid inlet(s) and said second gas inlet(s).

2. The valving arrangement of claim 1, further comprising a housing, said housing at least partially defining a liquid flow path connecting the liquid in the container to the first liquid inlet(s) and a separate gas flow path connecting the headspace with the second gas inlet(s).

3. The valving arrangement of claim 2, wherein a lower region of the valve stem locates within the housing and the seal is mounted on the housing for relative sliding engagement with the valve stem.

4. The valving arrangement of claim 1, wherein a cylindrical interface is formed between the seal and the valve stem.

5. The valving arrangement of claim 1, being adapted to discharge a gaseous propellant from the container that is a gas at a temperature of 25° C. and a pressure of at least 50 bar.

6. The valving arrangement of claim 1, wherein the at least one first liquid inlet extends at a non-normal angle relative to the flow conduit and the at least one second gas inlet extends transverse to the flow conduit.

* * * * *